(12) United States Patent
Honold et al.

(10) Patent No.: US 12,186,578 B2
(45) Date of Patent: Jan. 7, 2025

(54) PHOTOBIOMODULATION (PBM) IN GENERAL LIGHTING

(71) Applicant: Seaborough Life Science B.V., Amsterdam (NL)

(72) Inventors: Jürgen Eduard Honold, Amsterdam (NL); Martijn Jeroen Dekker, Groningen (NL)

(73) Assignee: Seaborough Life Science B.V., Amsterdam (NL)

( * ) Notice: Subject to any disclaimer, the term of this patent is extended or adjusted under 35 U.S.C. 154(b) by 709 days.

(21) Appl. No.: 17/312,970

(22) PCT Filed: Sep. 18, 2019

(86) PCT No.: PCT/EP2019/074984
§ 371 (c)(1),
(2) Date: Jun. 11, 2021

(87) PCT Pub. No.: WO2020/119965
PCT Pub. Date: Jun. 18, 2020

(65) Prior Publication Data
US 2022/0047887 A1 Feb. 17, 2022

(30) Foreign Application Priority Data
Dec. 13, 2018 (EP) .................... 18212476

(51) Int. Cl.
*A61N 5/06* (2006.01)
*H05B 45/20* (2020.01)
(52) U.S. Cl.
CPC ........... *A61N 5/0613* (2013.01); *H05B 45/20* (2020.01); *A61N 2005/0627* (2013.01);
(Continued)

(58) Field of Classification Search
CPC .......... A61N 5/0613; A61N 2005/0627; A61N 2005/0654; A61N 2005/0655;
(Continued)

(56) References Cited

U.S. PATENT DOCUMENTS 5,471,281 A 11/1995 Hayashi et al.
5,766,233 A * 6/1998 Thiberg ............... A61N 5/0616
607/88

(Continued)

FOREIGN PATENT DOCUMENTS

CN 103636006 A 3/2014
CN 207378643 U 5/2018
(Continued)

OTHER PUBLICATIONS

"Research on Infrared/White Light Hybrid Complementary Lighting in Intelligent Transportation", Dongdong Gao, Xiaoting Xu, Bo Li, Infrared and Laser Engineering, vol. 47, May 10, 2018, Issue 9.
(Continued)

*Primary Examiner* — Carl H Layno
*Assistant Examiner* — Aya Ziad Bakkar
(74) *Attorney, Agent, or Firm* — David P. Owen; Hoyng Rokh Monegier B.V.

(57) ABSTRACT

A lighting arrangement for providing visible light and radiation in another spectrum that is medically beneficial is provided. The lighting arrangement comprises a light source adapted to emit visible light; a radiation source adapted to emit radiation in a predetermined spectrum, and a driver circuit adapted to provide a first driving current that is pulsed and has a duty cycle of not greater than 20%. The predetermined spectrum is preferably in the range 760-1400 nm. The lighting arrangement is adapted to provide the first driving current to the radiation source but not the light
(Continued)

source. Corresponding method and products employing such lighting arrangement are also provided.

25 Claims, 16 Drawing Sheets

(52) U.S. Cl.
CPC .............. *A61N 2005/0654* (2013.01); *A61N 2005/0655* (2013.01); *A61N 2005/0659* (2013.01); *A61N 2005/0663* (2013.01)

(58) Field of Classification Search
CPC .... A61N 2005/0659; A61N 2005/0663; A61N 2005/0662; H05B 45/20
See application file for complete search history.

(56) References Cited

U.S. PATENT DOCUMENTS

| | | | |
|---|---|---|---|
| 8,760,370 B2 * | 6/2014 | Maxik | ............... G09G 5/02 349/71 |
| 2004/0036975 A1 | 2/2004 | Slatkine | |
| 2007/0219605 A1 * | 9/2007 | Yaroslavsky | ........ A61N 5/0613 607/88 |
| 2009/0054953 A1 | 2/2009 | Whitehurst | |
| 2010/0241110 A1 | 9/2010 | Solomon et al. | |
| 2011/0012503 A1 | 1/2011 | Jackson | |
| 2016/0317833 A1 | 11/2016 | Tedford et al. | |
| 2016/0375161 A1 | 12/2016 | Hawkins et al. | |
| 2018/0180226 A1 | 6/2018 | Van Bommel et al. | |
| 2018/0302961 A1 * | 10/2018 | Hagelaar | ................ H05B 45/20 |

FOREIGN PATENT DOCUMENTS

| | | | | |
|---|---|---|---|---|
| CN | 108519617 A | 9/2018 | | |
| JP | H9-508031 A | 8/1997 | | |
| JP | 2008-508918 A | 3/2008 | | |
| JP | 2017-528878 A | 9/2017 | | |
| SE | 9900076 | 1/1999 | | |
| WO | 1995019809 A | 7/1995 | | |
| WO | 0043069 A1 | 7/2000 | | |
| WO | 2006013390 A | 2/2006 | | |
| WO | 2006031753 A2 | 3/2006 | | |
| WO | 2011121481 A1 | 10/2011 | | |
| WO | 2016037994 A | 3/2016 | | |
| WO | 2017086880 A1 | 5/2017 | | |
| WO | WO-2018039433 A1 * | 3/2018 | ........ A61M 21/0094 | |

OTHER PUBLICATIONS

"Impact of SiO2 nanoparticles on the performance of remote fluorescent-based white LED devices", Ningze Zhuo, Na Zhang, Yuehua Zhu, et al., Aug. 26, 2016, China LED Lighting Forum Collected Papers.

"Short wave infrared SWIR) imaging systems using small Unmanned Aerial Systems (sUAS)", B. Stark, M. McGee and Y Chen, Jul. 9, 2015, International Conference on Unmanned Aircraft Systems (ICUAS).

* cited by examiner

Belviso C1 600 CDP LED3900nw 01
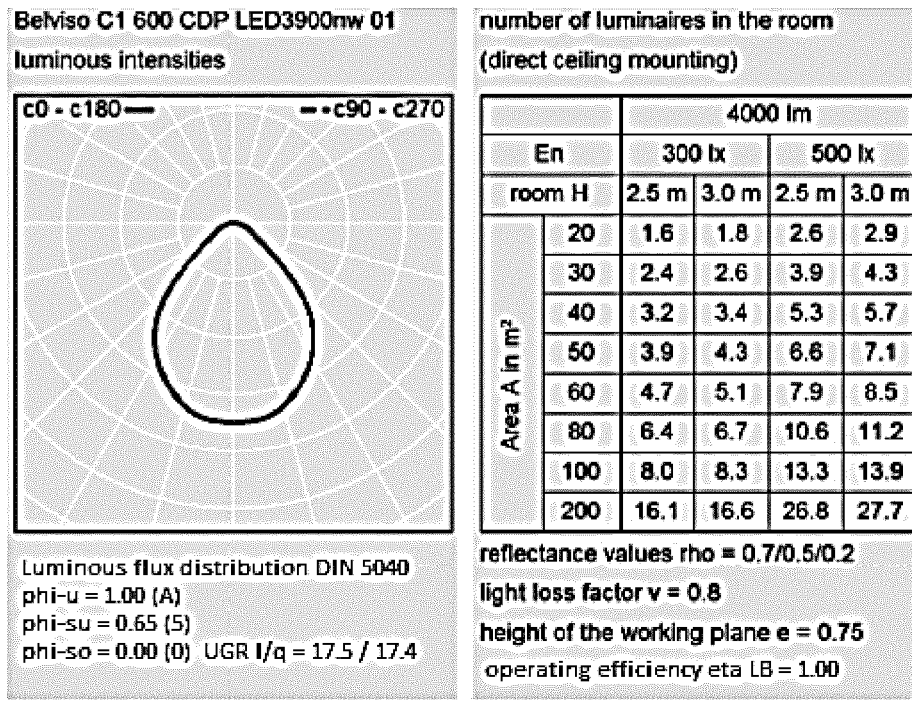
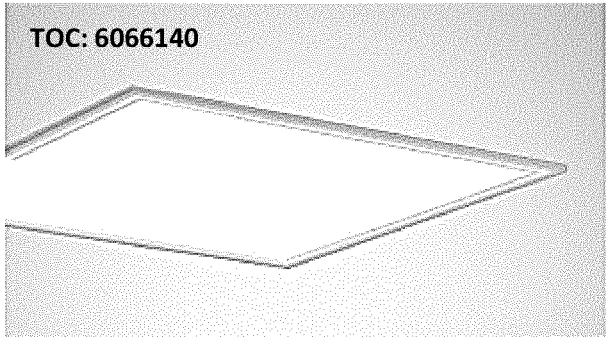
FIG. 8
LIGHT CALCULATOR
Lamp
Mounting method: Surface mounted
Luminaire luminous flux: 4.000 lm
Working plane
Height above ground: 0,75 m
Illuminance: 500 lx
Border areas of 0,5 m: Yes
Room
Dimensions: 5 x 4 x 3 m
Reflectance: 70/50/20
Maintenance factor: 0,8
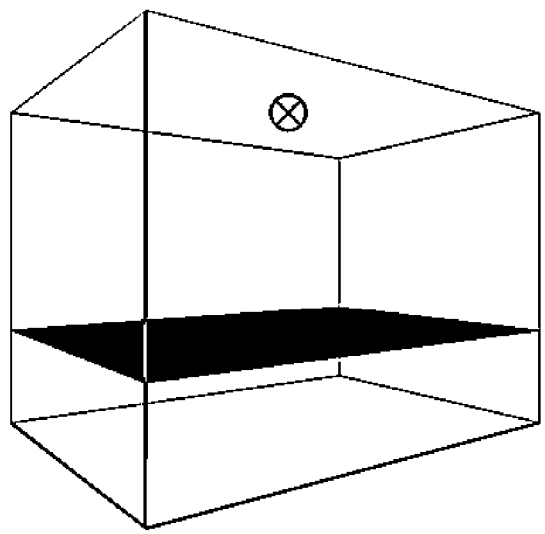

PHOTOBIOMODULATION (PBM) IN GENERAL LIGHTING

TECHNICAL FIELD

The invention relates generally to lighting, and more particularly to a lighting apparatus, a lighting system, and a method for providing a lighting apparatus that delivers radiation in a non-visible spectrum sufficient to induce photobiomodulation (PBM) response.

BACKGROUND ART

Photobiomodulation (PBM) involves irradiating a living organism at certain energy/power levels to induce biological or biochemical responses. The irradiation may be in the visible spectrum, such as red light, or in the non-visible spectrum, such as infrared (IR). There has been a significant amount of research about the medical benefits of employing PBM therapy to treat physical and psychological symptoms.

However, most of the equipment that administer PBM radiation are specialized devices that are only available at a very limited number of medical facilities. Moreover, these specialized devices are often so complicated that only a team of well-trained physicians, nurses and technicians can use them. These factors greatly limit the spread of the medical benefits of PBM within the general public.

Therefore, there is a need to overcome the abovementioned disadvantages of the currently available apparatuses and methods.

SUMMARY OF THE INVENTION

It would be desirable to provide an apparatus that is easy to use, energy efficient, cost effective and yet emits an amount of radiation sufficient to induce PBM response.

According to a first aspect of the present disclosure, a lighting arrangement is provided. The lighting arrangement may comprise a light source, a radiation source and a driver circuit. The light source may be adapted to emit visible light. In an embodiment, the light source may be capable of or suitable for emitting visible light having a color point in a CIE XYZ color space, which color point has a distance less than 10 Standard Deviation Color Matching (SDCM) to a black body line in said color space. The radiation source may be adapted to emit radiation in a predetermined spectrum. In an embodiment, the predetermined spectrum may be within the infrared band or in the range about 760-1400 nm. The predetermined spectrum may include a non-visible spectrum. The driver circuit may be adapted to provide a first driving current. The first driving current may be pulsed and may have a duty cycle of not greater than 20%. The lighting arrangement may be adapted to provide the first driving current to the radiation source but not the light source.

Traditional light sources already emit some radiation in the band that can induce PBM response in human. For example, the emission spectrum of common incandescent bulbs includes a small amount of red and near infrared light, two of the bands that have been associated with the ability to induce PBM response.

However, medical research indicates that the radiation needs to achieve a certain minimum amount of power density (measured in optical power per unit area) and dosage (measured in energy per unit area) within the PBM-inducing light spectrum before the radiation can induce a PBM response in the subject.

It is to be noted that the meaning of the word "light" alone in the present disclosure is not limited to visible light. The word "light" in the present disclosure may include electromagnetic radiation outside the visible light spectrum. By the same token, it is also to be noted that terms such as "optical power" are not limited to power of visible light.

The inventor noticed a surprising effect which was uncovered from analysis of research literature in the PBM field: photo-induced biological or biochemical responses may vary across power densities despite the same energy density or dosage (energy over unit area) being delivered. In other words, targeting the product of power and time (and power density and time) alone may be insufficient; appropriate combinations of power (density) and time matter. Sufficient power density, even if only for a short period, is needed to induce PBM response. Spreading the radiation over time to achieve the same amount of energy with a power density lower than a threshold may induce no or at most limited PBM response. That is, an insufficient power density is unlikely to be remedied by extending irradiation time.

The inventor recognized the problem that driving traditional light sources such as incandescent bulbs at a level that can provide sufficient power density at a certain distance in the PBM-inducing light spectrum would require an excessive amount of electrical power. This problem arises at least from the fact that the incandescent bulb is typically always on. Driving an incandescent bulb to provide sufficient power density in the PBM-inducing light spectrum would consume at least one order of magnitude more electrical power than is currently expected for sources for general lighting.

The inventor recognizes that recent advances in other light sources, such as solid-state lighting (SSL) technologies, could remedy the deficiency of incandescent bulbs. Lighting devices from SSL technologies, the light-emitting diode (LED) being an example, have lower heat emission and a narrower emission band, contributing to a higher energy efficiency. SSL devices also allow for a more precisely controlled emission band, enabling efficient power allocation in the desired emission bands. More importantly, SSL devices are capable of reacting rapidly to driving and/or control signals. In other words, timing control with SSL devices is much more precise compared to other types of light sources, such as incandescent or halogen bulbs, which, being thermal emitters, have thermal inertia. To put it differently, SSL devices allow for nearly instant reaction to control and/or driving signals with negligible delay, making them suitable for rapid pulsing.

However, the inventor also recognizes that current SSL devices alone still fail to deliver the necessary amount of power density and dosage within the PBM-inducing band. For example, assume that a linear lamp of e.g. T8 or T5 type with a length of 150 cm and equipped with LED devices as a replacement for a fluorescent tube has a homogeneous light distribution over 180°. At a distance r=2 m from the lamp, the surface of a theoretical half-cylinder, which represents the theoretical light distribution at the distance of 2 m, is A=πrh=~10 m². Assume that the linear lamp is equipped with LED devices emitting substantially constant radiation over time with a total output power of 1 W in the desired light spectrum, then an average power density at an average distance of 2 m from the lamp is about 10 μW/cm² (0.1 W/m²), which is orders of magnitude below the required minimum power density suggested by recent medical research, e.g., 1-50 mW/cm². Note that since the difference is orders of magnitude, it could be impractical and very likely economically unacceptable to keep the LED devices emitting substantially constant radiation over time and increase the total emitted Watts by the corresponding orders of magnitude.

The inventor recognizes another possibility to achieve the required amount of power density within the physical capabilities of current SSL devices. By driving an SSL device, such as an LED, with a pulse instead of a continuous wave (which may be abbreviated as "CW" and implies non-pulsed) or nearly continuous wave signal, it is possible to boost the peak power emitted by the SSL device by a factor of the inverse of the duty cycle of the pulse while consuming the same amount of electric power. In other words, an SSL device with pulsed emission can achieve a much higher peak emission power than the same device with continuous wave (CW) emission. To put it differently, the inventor recognized the ability of pulsing to efficiently utilize the limited amount of electrical power to emit radiation with the required amount of (short-term) power. In other words, the inventor recognized that while narrow-band emission devices such as SSL devices allow for concentrating a limited amount of power into only the desired spectrum, pulsing such narrow-band emission devices further allows concentrating the available power into a short duration to enable such devices to emit radiation that passes an elevated power threshold. Another advantage of pulsing is that the emission device can cool down between the pulses. This may alleviate the thermal budget of the emission device and may allow, e.g., a smaller driver circuit and the use of a smaller and less costly SSL device (i.e., with less epitaxial materials and/or smaller die surfaces). The cost-saving may come from using smaller and cheaper SSL devices and/or using fewer number of SSL devices in a lighting arrangement that provides a given amount of PBM-inducing radiation. A more relaxed thermal budget may also reduce the size of the housing that accommodates the emission device and the size of any associated cooling device.

For example, we assume that an optical power emission of 500 W with a peak wavelength of 850 nm light is required to enable a power density of 8 mW/cm$^2$ of the light at a 2 m distance from the emission source. Instead of using a 500 W continuous wave emitter (i.e., emitting non-pulsed waves at substantially constant power over time), the target power density of 8 mW/cm$^2$ at 2 m distance from the emission source can also be achieved by a pulsed 500 W emitter with lower electrical power consumption. For example, the electrical power consumption will be 500 times lower compared with continuous wave emission if the emitted radiation is pulsed (or if the emitter is driven so as to emit radiation) at a pulse frequency of 1 Hz and a pulse duration of 2 ms (namely, a duty cycle of 0.2%). The average optical power in the pulsed mode will now be 1 W instead of 500 W because the radiation is present during $\frac{1}{500}$ of a second. Due to the reduction of the average optical power emission by the factor of 500 by the means of pulsing in the pulse frequency and pulse duration, the electrical power consumption will also be lowered by the same factor 500 (assuming a similar efficiency of a continuous wave electronic driver unit and emitter compared with a pulse mode electronic driver unit and emitter).

The cost-saving benefit of pulsing the radiation source is further elaborated here. The maximum driving current of several types of radiation sources, such as light emitting diodes, is constrained by thermal requirements: too much driving would overheat the diodes and reduce radiation efficiency. If the lighting arrangement needs to output an amount of PBM-inducing radiation that is more than can be provided by the permissible driving current of the radiation source, then either a larger quantity of the radiation sources is required, or the type of the radiation source has to change. Both options can be costly. However, if the radiation source is pulsed, then the permissible driving current can further increase because the radiation source can cool down between the pulses. In other words, pulsing allows a given radiation source to push up, or enhance, its amount of permissible driving current. This allows using smaller and cheaper radiation sources and/or fewer number of them in a lighting arrangement that provides a given amount of PBM-inducing radiation. In an embodiment, the radiation source and driver unit are adapted to operate in a drive mode with an enhanced permissible driving current.

In the context of this document, a radiation source is driven with an enhanced permissible driving current if the driving current during a pulse exceeds the permissible driving current at DC as specified by the manufacturer. In the example where the radiation source is an infrared LED, the manufacturer typically specifies a maximum rating for the forward current, such as 1 A DC. The maximum rating at DC (in continuous wave driving mode) does not mean that this maximum rating can never be exceeded; it means that such maximum rating cannot be exceeded in continuous wave driving mode without adverse consequences to at least one aspect of the performance of the radiation source, be it electrical, thermal or optical. The manufacturer may also specify for how long the maximum rating may be exceeded and by how much. In the example of the infrared LED, the manufacturer may specify the "pulse handling capability" of the LED, which states the relationship between the amount of forward current exceeding the maximum rating at DC and the length of permissible pulse time and duty cycle at such forward current.

Once a general lighting apparatus is adapted to emit a sufficient amount of power to enable a certain power density at a certain distance that may induce PBM responses, many advantages materialize. The general lighting apparatus, such as a lamp or overhead lighting, is easy to use and commonly available, and therefore the need for medical specialists to administer PBM radiation is greatly reduced, which amounts to a significant saving of time and financial resources of the recipient of PBM radiation.

Note that the same adaptation may be made to a task lighting apparatus or an accent lighting apparatus. Task lighting may be viewed as a specialized form of general lighting in that both illuminate to assist human vision but that task lighting may be used in places with special illumination requirements, such as sport fields and streets (which need high brightness over a large area). Accent lighting may be intended to build a visual accent and create a point of interest for the viewer; common applications include accentuating houseplants, sculptures, painting and other decorations, and emphasizing architectural textures or outdoor landscaping. The general, task or accent lighting apparatuses that may be used in embodiments of the present disclosure include, but are not limited to, a light emitting surface that might be installed in or be part of a luminaire or fixture for an area, such as overhead lighting, bedhead lighting, kitchen lighting, sport lighting, street lighting, healthcare lighting, public lighting, bathroom lighting, vanity lighting, track lighting and mirror lighting. The applicable lighting apparatuses also include illumination devices that illuminates spaces, areas and surfaces and thereby brightens the environment in which people and animals spend time.

In addition to the abovementioned advantages, a user can stay naturally in or be exposed naturally to the light of a general lighting or task lighting or accent lighting apparatus for a long time without his activities being interrupted. This brings about the flexibility in providing a wide range of dosage, measured in energy per unit area. Recall that energy is power multiplied by time. This means that different amount of dosages can be easily achieved simply by turning on the general lighting or task lighting or accent lighting apparatus. The simplicity of dosing is achieved by spreading an average daily dose over many hours, so that the applied dose never exceeds the recommended dose. The spreading of the dose over a long period of time at a power density effective for inducing PBM responses is achieved by the pulsing method described in this document. Whereas a visit of more than 30 minutes to a specialist treatment center will often be considered bothersome, it is entirely common to stay under or be exposed to the light of a general lighting apparatus for more than one hour or even eight hours without the person feeling bothered at all.

For example, assume a general lighting apparatus that includes an infrared light emitter having a peak emission of 850 nm and emitting in a pulsed mode at a pulse frequency of 1 Hz and a pulse duration of 2 ms. Also assume that the infrared light emitter has a peak optical emission power of 500 W and hence can deliver 8 $mW/cm^2$ to a location 2 m away from the emitter. Then, the light emitter could deliver an energy density accumulated over eight hours of roughly 0.23 $J/cm^2$ (8 $mW/cm^2$ multiplied by 8*60*60 seconds) to that location.

Note that in the embodiment where the light source is capable of or suitable for emitting visible light having a color point that has a distance less than 10 SDCM to a black body line in a CIE XYZ color space, such light source is suitable for being used in a general lighting apparatus. The reason is that the visible light emitted by such light source is relatively white in the sense that this kind of visible light is suitable for raising the illumination level of a space to assist human vision and/or to make it more convenient for people to live and/or work in that space. In some embodiments, the light source is capable of or suitable for emitting visible light having a color point that has a distance less than 10 SDCM to a black body line in a CIE XYZ color space. In some embodiments, the distance may be less than 8 SDCM, 7 SDCM, 6 SDCM, 5 SDCM or 3 SDCM to the black body line in the CIE XYZ color space.

Note that pulsing the radiation sources to provide radiation that may induce PBM responses (e.g., in the NIR band) at appropriate duration and/or period may greatly reduce the chance of overdosing even if the user stays close to the general lighting apparatus for a period much longer than a typical treatment period of 30 or 60 minutes at a specialist center. For example, some medical research suggests that the beneficial biological response increases with increasing dosage and peaks at about 10 $J/cm^2$. Further increasing dosage may decreases beneficial PBM responses and may even cease to be beneficial if the dosage exceeds about 35 $J/cm^2$. Thus, if a user is exposed to a power density level of about 8 $mW/cm^2$ more than about 20 minutes, then it would be hard for the user to receive the peak benefit. In other words, sufficiently short pulse duration and/or period may provide sufficient power density to induce PBM responses and at the same time deliver a beneficial amount of total energy density (which is power per unit area multiplied by time) over a wide range of time, e.g., from a few minutes up to 8 hours or more, without overdosing the user. That way, the user may use the lighting apparatus as if it were a conventional light source without any need to worry about when to switch it off (to prevent overdosage) and yet can still receive the benefit of PBM-inducing radiation.

Another benefit of pulsing the radiation sources is better safety to the user's eyes through decreased thermal load induced by such radiation in relevant spectrum in the corneas of the user's eyes, which in turn results from an average power density of the pulsed radiation that is sufficiently low to comply with relevant safety regulations and safety limits. For example, IEC 62471, a common international standard, requires that a lamp intended for general lighting service (GLS) should keep the ocular exposure of the user to infrared radiation over the wavelength range 780 nm to 3000 nm for times greater than 1000 s at a distance where the lamp produces an illuminance of 500 lux to be less than 10 $mW/cm^2$ (100 $W/m^2$). A lighting arrangement whose infrared radiation source produces a power density of 20 $mW/cm^2$, for example, at a distance where 500 lux is produced by the lighting arrangement may satisfy this safety requirement by pulsing the infrared radiation source at a duty cycle of 50% according to the methods described in this document. As another example, IEC 62471 requires that a pulsed lamp source should keep the infrared ocular exposure for times greater than 1000 s at a distance of 200 mm to be less than 10 $mW/cm^2$. Therefore, a pulsed radiation source that emits only infrared radiation and produces 8 $mW/cm^2$ at 2 m, equivalent to 800 $mW/cm^2$ at 0.2 m assuming the radiation is emitted omni-directionally and spread evenly, may become compliant by pulsing the infrared radiation source at a duty cycle of 1.25%. Therefore, the technical solution of pulsing the radiation source (such as an infrared source) as described in this document enables to use general lighting devices where the (infrared) radiation source may be used without being combined with visible light emitters. For example, photobiological stimulation may be induced at night without visible light disturbing the user's sleep. In the above mentioned safety context, the pulsing of the (infrared) radiation source is also an enabling element that makes the PBM application safe and compliant with IEC 62471 at times where the visible component of the emitted spectrum gets dimmed to a lower illumination level.

Therefore, a lighting arrangement according to the inventive idea behind the first aspect of the present disclosure is able to elicit certain local and systemic (body-wide) PBM effects. For example, there is a wide variety of medical research literature suggesting that PBM may stimulate, heal, regenerate, and protect human tissue that has either been injured, is degenerating, or else at risk of dying. Most importantly, PBM may induce an anti-inflammatory, anti-oxidative and/or mitochondria-boosting and normalizing effect to the human body and its systems. The positive effects on the human body further may be described as bio-stimulating and antiallergic; further immunomodulation, vasodilation of blood vessels and antihypoxic to the blood. Other positive effects may include the stimulation of the brain to regenerate, for example after suffering an ischemic stroke, or to increase the cognitive functions of healthy subjects. It further has been suggested by the latest research that PBM may induce positive effects on the mental constitution of persons suffering, e.g., depression, dementia, Alzheimer, Parkinson, ADHD, ADD, Hypertension, testosterone deficiency and PTSD. Further, skin rejuvenation and a decrease of skin aging may be achieved, and certain systemic effects which may be described as rejuvenation or the deacceleration of aging of the human body as a whole. Further preconditioning of the skin or the body as a whole, to prepare for certain kinds of stress, for example before extended sunbaths, or as a preconditioning before expected high levels of stress like extensive sport, mental stress, or stress to the human body which is related to high levels of reactive oxygen species, or as a preconditioning before being exposed to potentially toxic environments, or where direct contact with toxins may be expected. Further, it may be used to decrease recovery time after being exposed to extensive sport, mental stress, harmful levels of radiation or toxins. It may also have positive long-term effects on the eye-vision and general health of the human eye, and may accelerate and improve hair growth. Further, it may help to normalize melatonin levels in the human body and therefore improve sleep. It also may help dealing with jetlag, or other circumstances where the circadian rhythm is unbalanced. To sum it up, due to the fundamental, positive PBM effects on eukaryotic cells, inducing an anti-inflammatory, anti-oxidative, homeostatic and/or mitochondria-boosting and normalizing effect, positive effects may be achieved in any part of the human body. Some of the mentioned benefits may also be applicable in a similar way to animals, like pets (e.g. dogs, cats) or farm animals (e.g. cows, horses, pigs); basically, all beings made of eukaryotic cells may have benefits from being exposed to certain light which causes PBM effects.

Another advantage of the lighting arrangement according to the inventive idea behind the first aspect of the present disclosure is the ability to provide general, task or accent lighting and PBM-inducing radiation at the same time. The same lighting arrangement provides both functions.

In an embodiment, the predetermined spectrum of the radiation emitted by the radiation source may be in the range 800-1100 nm. The predetermined spectrum may preferably be in the range 800-870 nm. In an embodiment, the predetermined spectrum may be in the range 800-1100 nm with optionally a peak emission around 830, 980 and/or 1060 nm. In an embodiment, the predetermined spectrum may be in the range 800-870 nm with optionally a peak emission within the range 820-850 nm. There has been a rich literature demonstrating the therapeutic value of PBM in the infrared band, and the inventor recognized that ranges such as 800-1100 nm and 800-870 nm may be particularly beneficial and/or easy to implement, which makes these embodiments particularly useful.

In an embodiment, the predetermined spectrum may exclude a visible spectrum or does not include a visible spectrum. Since the pulsed emission is not within the visible spectrum, the pulses can have very high peak emission without causing any perceptible annoyances to the user.

In an embodiment, the lighting arrangement may be adapted to provide a second driving current different from the first driving current to the light source. The second driving current may drive the light source. In an embodiment, the second driving current may be a direct current (DC) or an alternating current (AC) or a pulse-width modulated (PWM) current. The PWM current may preferably have a pulse frequency in the range 20000 Hz-300000 Hz. The second driving current may provide more flexibility in driving the light source that is adapted to emit visible light. In other words, the (visible) light source may be easily driven in a manner different from the radiation source that is adapted to emit radiation in the predetermined spectrum. Driving the visible light source with DC or AC may further increase the stability of the visible light emitted by the light source. Driving the visible light source with pulse-width modulation (PWM) signals may, for example, be used to achieve brightness dimming Such driving currents may be well suitable for widely used light sources, such as incandescent bulbs, fluorescent tubes and different kinds of LEDs.

In an embodiment, the driver circuit may be a first driver circuit. The lighting arrangement may further comprise a second driver circuit adapted to provide the second driving current. Separating the driver circuits for energizing the light source and the radiation source may help prevent one driver circuit from interfering with the light source or radiation source that the one driver circuit is not energizing.

In an embodiment, the pulse duration of the first driving current may be in the range of about 0.05-500 ms. The pulse duration of the first driving current may optionally be in the range of about 0.1-100 ms, preferably about 0.5-20 ms, most preferably about 4-10 ms. Other optional ranges for the pulse duration may include 1-40 ms, 4-40 ms and 8-30 ms. These embodiments may have the advantageous effects of practical implementation with available electronics and particular benefits for certain ranges according to the research literature. On the one hand, longer pulses may provide better PBM responses; on the other hand, shorter pulses and/or a lower duty cycle may enhance the permissible driving current of the radiation source.

In an embodiment, the pulse frequency of the first driving current may be in the range of about 0.01-10000 Hz. The pulse frequency of the first driving current may optionally be in the range of about 0.1-2500 Hz, preferably about 1-160 Hz. This embodiment may have the advantageous effects of practical implementation with available electronics and particular benefits for certain ranges according to the research literature.

In an embodiment, the first driving current may have a duty cycle of not greater than 10%, optionally not greater than 5%, optionally not greater than 1%. A lower duty cycle may allow the radiation source to generate higher (peak) emission power with the same amount of consumed electrical power. A lower or more fine-tuned duty cycle may also help reduce the chance of overdosing the user. In an embodiment, the first driving current may have alternating duty cycles, such as a first duty cycle of 1% during a predetermined period and a second duty cycle of 2% during another predetermined period. A plurality of duty cycles may increase the flexibility in programming the dose of PBM-inducing radiation at different times.

Of course, combinations of different ranges of pulse duration and pulse frequency are possible. Note also that a desired (peak) emission power from the radiation source with varying amounts of consumed electrical power may be achieved by changing the pulse duration, the pulse frequency or both. This flexibility may allow different forms of power and/or dosage and/or electrical power consumption control that can be adjusted to meet particular needs.

In an embodiment, at least one of the pulse duration, the pulse frequency and the duty cycle are so selected as to enable the first driving current to drive the radiation source with an enhanced permissible driving current. Driving the radiation source with an enhanced permissible driving current could enable a given amount of radiated power density and dosage with less costly radiation sources, which may have less permissible drive ratings at DC, or a fewer number of a given type of radiation source, which can operate at a higher driving condition to achieve the same radiation output, or both. This could reduce the cost of the lighting arrangement.

In an embodiment, one pulse may be split into a plurality of "sub"-pulses. For example, assume a pulse duration of 10 ms and a pulse period of 100 ms (e.g., a pulse frequency of 10 Hz). It may be that one "main" pulse of 10 ms is split into sub-pulses with 80 ns pulse duration and a pulse period of 100 ns. In this event, the main pulse comprises 100 sub-pulses. It is noted that the pulse duration of the sub-pulses is not particularly limited so long as it is shorter than the pulse duration of the main-pulse. Pulsing at different levels of pulse duration and/or pulse frequency provides further flexibility in adjusting the radiation pattern to suit a particular usage need or to adapt with a particular requirement in the associated electronics.

In an embodiment, the radiation source may be adapted to generate radiation in the predetermined spectrum which may be pulsed. The radiation in the predetermined spectrum (e.g., a spectrum that is capable of inducing PBM responses) is pulsed. Pulsing may allow the peak emission power of the radiation source be "boosted" by a desirable factor at the same amount of electrical power consumption. Pulsing may also extend the time that a user may be exposed to PBM-inducing radiation without being overdosed.

In an embodiment, a peak emission power of the radiation emitted by the radiation source energized by the pulsed first driving current may be at least 25 W, optionally at least 100 W, optionally at least 200 W, optionally at least 500 W. A peak emission power of at least 25 W may enable at least 1 mW/cm² measured at about 0.6 m from the lighting arrangement with a radiation pattern of a half-sphere and could ensure the user using such lighting arrangement in, e.g., a desk lamp, to receive sufficient power density. A higher peak emission power could let the user still be exposed to sufficient power density even if the user is further away from the lighting arrangement and/or the radiation pattern differs. For example, a peak emission power of at least 200 W may enable at least 1 mW/cm² measured at, e.g., 1.8 m from the lighting arrangement with a radiation pattern of, e.g., half-sphere. This may suit other common usage scenarios of a general lighting apparatus, such as in an office setting.

In an embodiment, a peak emission power of the radiation emitted by the radiation source receiving the pulsed first driving current may be sufficient to induce photobiomodulation (PBM) response in a human body. This would provide added-value over other general lighting apparatuses with merely a traditional light source.

In an embodiment, a peak emission power of the radiation source receiving the pulsed first driving current may enable a power density of 0.4-50 mW/cm², optionally 5-15 mW/cm², measured at a common average distance of between about 0.2 and about 5 m from the radiation source. The common average distance may optionally be between about 0.5 and about 3 m from the radiation source. The common average distance may optionally be about 2 m. The advantageous effects include research-proven PBM responses beneficial to the human body, where 0.4 mW/cm² may be sufficient to start inducing PBM responses through the eyes. Such common average distances may also be suitable for many usage scenarios.

In an embodiment, a peak emission power of the radiation source receiving the pulsed first driving current may enable a power density of 0.4-50 mW/cm², optionally 5-15 mW/cm², measured at a distance where the illuminance of the lighting device is about 500 Lux (lx).

In an embodiment, the radiation source may emit at least 3,000 Joule in the pre-determined spectrum within 8 hours.

In an embodiment, the radiation source receiving the pulsed first driving current may be configured to deliver a dosage (energy per unit area) that is sufficient to induce PBM response in a human body. In an embodiment, the radiation source receiving the pulsed first driving current may be configured to deliver a dosage of 0.01-5 J/cm² measured at a common average distance from the radiation source, where the common average distance from the radiation source may be between about 0.2 and about 5 m. The common average distance from the radiation source may optionally be between about 0.5 and about 3 m, preferably at about 2 m. The advantageous effects include research-proven PBM responses beneficial to the human body. Such common average distances may also be suitable for many usage scenarios.

In an embodiment, the dosage may be regulated by modifying at least one of an amplitude, a pulse duration, a pulse frequency and a duty cycle of the first driving current. Preferably, the pulse frequency is modified while the pulse duration stays substantially the same. This may be preferred over changing the pulse duration, which may exacerbate the drooping effect of the epitaxial materials in the radiation source when the pulse lengths is increased due to the increased thermal load in the radiation emitting epitaxial materials. Modifying the pulse frequency may also be preferred over changing the amplitude because too low an amplitude may decrease the delivered power density during the pulse by so much as to reduce the efficacy of inducing PBM responses in the user. An exemplary threshold for maintaining the efficacy is at least 0.4 mW/cm² of NIR light, e.g., in between 800-870 nm, at a distance from the user to the lighting arrangement where the illuminance of the lighting arrangement reaches about 500 Lux.

In an embodiment, the radiation source in use may consume root mean square (RMS) electrical power of less than 50 W, optionally less than 25 W, optionally less than 10 W. Such levels of power consumption may be well suited for common daily usages and, in view of the ever-increasing environmental consciousness, may help the lighting arrangement meet various different energy consumption regulations. In an embodiment, the radiation source in use may consume a root mean square (RMS) electrical power per square meter of intentionally irradiated surface of less than 10 W, optionally less than 2 W, optionally less than 0.5 W. The RMS electrical power per square meter may be a useful metric for certain lighting applications where large areas are illuminated, such as sport field lighting.

In an embodiment, the radiation source may comprise a solid-state device. The solid-state device may be a LED, optionally more than one LED. These devices are readily available and come in a wide variety. In an embodiment, the solid-state device may be a flip-chip LED, which may offer better thermal performance and hence higher capability of enhanced permissible driving currents. The direct electrical bonding of the flip-chip LED to the mounting board may also let more current flow through, thereby offering a higher degree of enhanced permissible driving currents (i.e., a higher crest factor) should a large enhanced permissible driving current become useful.

In an embodiment, the lighting arrangement may be adapted to generate visible light from the light source having a luminous flux which does not have an %-flicker of more than 40%, preferably does not have an %-flicker of more than 20%, when the light source is in use. The limited amount of fluctuation in the luminous flux of the light source may increase the comfort of the user of the lighting arrangement (or general lighting apparatuses incorporating such lighting arrangements). In an embodiment, the lighting arrangement may be adapted to generate visible light from the light source without perceptible flicker to the human eye. The lack of flicker perceptible to the human eye may increase the user satisfaction with the lighting arrangement (or general lighting apparatuses incorporating such lighting arrangements).

In an embodiment, the light source may emit at least 250 lumens, optionally at least 1000 lumens, optionally at least 2000 lumens. In an embodiment, the correlated color temperature of the light source may be in the range 1700-6500K, optionally in the range 2400-5500K. In an embodiment, the color rendering index of the light source may be in the range 80-99 at a correlated color temperature of about 2700K. Such light sources satisfy many requirements for general lighting purposes, such as brightness, light color and color rendition, making the lighting arrangement of the embodiment of the present disclosure particularly convenient to and acceptable by general consumers. Needless to say, many suitable combinations of the lumens specification, the CCT and the CRI may be possible. For example, the light source may be a light troffer, which is a rectangular light fixture that fits into a modular dropped ceiling grid (i.e. 600×600 mm, or 300×1200 mm). Troffer fixtures have typically been designed to accommodate standard fluorescent lamps (e.g. T12, T8 or T5), but are now often designed with integral LED sources. In this example, the troffer fixture emits 4000 Lumen at a color temperature of 4000K with a CRI of 80.

In an embodiment, the light source may consume an electric power of less than 120 W, preferably less than 80 W, more preferably less than 30 W. Such power consumption may be particularly suitable for household and office usages.

In an embodiment, the light source may comprise a solid-state device. The solid-state device may comprise a LED, optionally more than one LED.

In an embodiment, a ratio of an electrical power consumed by the radiation source to an electrical power consumed by the light source when the lighting arrangement is in use may be not greater than 50%, preferably not greater than 25%, more preferably not greater than 10%, yet more preferably not greater than 5%. In an embodiment, the electric power consumed by the radiation source may be less than the electric power consumed by the light source, preferably less than two-thirds of the electric power consumed by the light source, more preferably less than one-fifth of the electric power consumed by the light source, yet more preferably in a range of about 4-11% of the electric power consumed by the light source. Since the radiation source consumes less electric power than the light source, the additional energy cost from the radiation source may be limited. In some embodiments, a user may hardly notice any difference in the energy bills that is attributed to the additional amount of electric power consumed by the radiation source.

In an embodiment, the driver circuit is adapted to modify the first driving current in response to an input to the driver circuit. The input may be from an awareness sensor that is coupled to the driver circuit and adapted to turn on or off the first driving current depending on whether the awareness sensor detects the presence of a user in its vicinity. The input may be from a distance sensor that is coupled to the driver circuit and adapted to turn on or off the first driving current depending on the detected distance from the user. Another source of the input may be data relating to the time of day, the ambient brightness, the season, and/or the weather, remotely provided to the driver circuit or other circuity that controls the driver circuit that may modify the first driving current to control the amount of the radiation delivered to the user. For example, the pulse frequency and thereby the radiation dose may increase on days with low ambient light, at night, in winter, and/or on dull overcast days when the user is exposed to less sunshine, and decrease on days with higher ambient light, in summer, and/or on bright sunny days. Any aspect of the first driving current that affect the amount of delivered radiation dose may be modified, such as the pulse amplitude, pulse period, pulse frequency and duty cycle. Yet another source of input may be user data supplied by, e.g., the user's smart mobile device, which may determine, for example, the amount of time the user stays indoor and then modifies the first driving current accordingly to increase or decrease the delivered radiation dose. In addition to the radiation dose, the power density may also be modified. The power density may be lowered, for example by reducing the amount of current flowing through the epitaxial material of the radiation source. The purposes may include targeting certain specific photobiological effects without stimulating other photobiological effects. One example is to target the retina of the human eye. The retina reacts to lower power densities than the human skin because, unlike the human skin, the human eye doesn't have a substantially light absorbing layer on the surface. Another reason for modifying the power density may be that the lighting arrangement is aware of its potentially variable distances from the user via positioning systems or awareness sensors or the like. Such positioning systems or sensors may be part of the lighting arrangement, or exist in smart devices or other devices located at or nearby the user's body. The ability to keep a substantially constant amount of power density delivered to the user's body at variable distances between the lighting arrangement and the user may help maintain a stable delivery of effective amounts of power density to the user's body surface. The improved stability in the delivery of effective amounts of power density may help optimize the photobiological stimulation of specific biological effects.

According to another aspect of the present disclosure, a lighting method is provided. The light method may comprise: providing a light source that may be adapted to emit visible light; providing a radiation source that may be adapted to emit radiation in a predetermined spectrum; and supplying a first driving current that may be pulsed and may have a duty cycle of not greater than 20% to the radiation source to generate radiation in the predetermined spectrum. The light source may be capable of emitting visible light having a color point in a CIE XYZ color space, wherein the color point has a distance less than 10 Standard Deviation Color Matching (SDCM) to a black body line in said color space. The predetermined spectrum may be within the infrared band. The predetermined spectrum may be in the range about 760-1400 nm. The first driving current may be not supplied to the light source. The duty cycle may be not greater than 20%. By sophisticated pulsing of the radiation source, an appropriate and beneficial amount of radiation in a predetermined spectrum may be provided at a reasonable amount of power consumption. Combining such radiation source into a general lighting apparatus may greatly expand it use and may turn it into a general lighting source with medical benefits that is easy to use. In addition, the method may have similar embodiments with similar effects and advantages as the embodiments of the above-discussed lighting arrangements.

According to another aspect of the present disclosure, a lamp for general lighting is provided. The lamp for general lighting may comprise one of the above-discussed lighting arrangements. In summary, such a lamp for general lighting may provide a dual-function visible light source.

According to another aspect of the present disclosure, a retrofit light bulb for general lighting is provided. The retrofit light bulb may comprise one of the above-discussed lighting arrangements. In summary, such a retrofit light bulb may provide general lighting and medical benefits. The retrofit light bulb may be particularly suitable for working with existing fixture bodies.

According to another aspect of the present disclosure, a retrofit light tube is provided. The retro fit light tube may comprise one of the above-discussed lighting arrangements. In summary, such a retrofit light tube may provide general lighting and medical benefits. The retrofit light tube may be particularly suitable for working with existing fixture bodies.

According to another aspect of the present disclosure, a luminaire is provided. The luminaire may comprise one of the above-discussed lighting arrangements. In summary, such a luminaire may provide general lighting and medical benefits.

Other embodiments of lighting arrangements, light methods, lamps, retrofit light bulbs, retrofit light tubes and luminaires according to the present disclosure are given in the appended claims, disclosure of which is incorporated herein by reference.

It is evident that the various embodiments described and explained above are mutual compatible with each other, unless explicitly stated. As such, the combination of any number of the features from the above embodiments is still within the present disclosure. For example, different combinations of exemplary predetermined spectrums, exemplary (peak) emission power levels of the radiation source and exemplary brightness of the light source are clearly within the scope of the present disclosure. Additionally, the features in the above embodiments may be disclaimed or otherwise left out. For example, the predetermined spectrum may have different emission peaks and valleys in the exemplary range 800-1100 nm. Likewise, the CCT may comprise discrete subranges within a particular exemplary range such as 1700-6500K. Such variations are still clearly within the scope of the present disclosure.

BRIEF DESCRIPTION OF THE DRAWINGS

Embodiments will now be described, by way of example only, with reference to the accompanying schematic drawings in which corresponding reference symbols indicate corresponding parts, and in which:

FIG. 8 provides an exemplary illustration of a troffer that may be used in conjunction with an embodiment of the present disclosure.

The figures are meant for illustrative purposes only, and do not serve as restriction of the scope or the protection as laid down by the claims.

DESCRIPTION OF ILLUSTRATIVE EMBODIMENTS

The following is a description of certain embodiments of the invention, given by way of example only and with reference to the drawings.

Figure 1A:
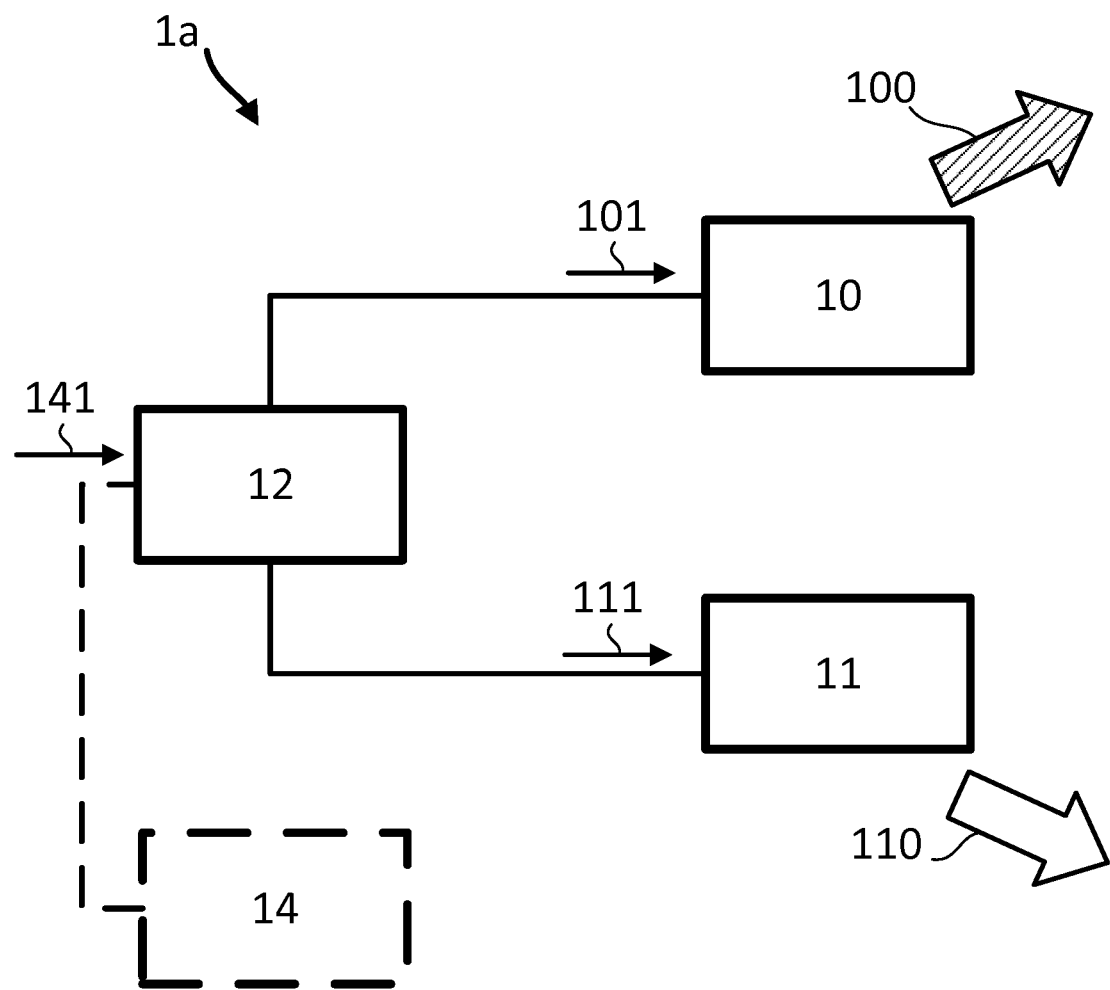
FIG. 1A schematically shows a lighting arrangement in accordance with an embodiment of the present disclosure.

Referring to FIG. 1A, which illustrates a lighting arrangement (which may also be referred to as a "lighting assembly") 1a in accordance with an embodiment of the present disclosure. The lighting arrangement 1a comprises a radiation source 10, a light source 11 and a driver circuit 12. Optionally, the lighting arrangement 1a may comprise a sensor 14 coupled to the driver circuit 12.

The radiation source 10 is adapted to emit radiation 100 in a predetermined spectrum that includes a non-visible spectrum. The radiation source 10 emits radiation 100 upon receiving or being energized by a driving signal. The driving signal may be an electric signal. In an embodiment, the driving signal is an electric current, such as a first driving current 101.

The predetermined spectrum is not limited to the non-visible spectrum and may optionally comprise a portion of the visible spectrum. In an embodiment, the predetermined spectrum comprises the infrared (IR) spectrum and may optionally also include light in the red (visible) spectrum. In an embodiment, the predetermined spectrum is within the IR spectrum, optionally the near infrared (NIR) spectrum. In an embodiment, the predetermined spectrum may be in the range 760-1400 nm. The predetermined spectrum may optionally be in the range 800-1100 nm. Another option is the range 800-870 nm. In an embodiment, the predetermined spectrum does not include a visible spectrum.

Recent advances in medical research have demonstrated that irradiating a living organism with radiation comprising the IR spectrum and/or red light at certain energy/power levels may induce beneficial biological or biochemical responses. Such irradiation is often referred to as photobiomodulation (PBM). Available medical research results on the medical benefits of employing PBM therapy to treat physical and psychological symptoms are rapidly increasing. Some wavelengths that have attracted particular attention include 606, 627, 630, 632.8, 640, 660, and 670 nm (in the red region) and 785, 800, 804, 808, 810, 820, 830, 850, 904, 980 and 1060 nm (in the NIR region). Some spectrums that have attracted particular attention include 650-680 and 800-870 nm.

In an embodiment, the predetermined spectrum is in the range 800-1100 nm with an optional peak emission around 830 nm. Other optional peak emissions include 980 and/or 1060 nm. In an embodiment, the predetermined spectrum is in the range 800-870 nm with an optional peak emission within the range 820-850 nm.

In an embodiment, the radiation source 10 may comprise a solid-state device. In an embodiment, the radiation source 10 may comprise a light-emitting diode (LED) and optionally more than one LED. In an embodiment, the radiation source 10 may comprise an LED emitting in the NIR region.

The radiation source 10, when in use, may consume electrical power. There is no particular limit to the amount of electrical power that the radiation source 10 may consume, so long as it is within the limit of the physical capabilities of the devices used in the radiation source 10. In an embodiment, the radiation source 10 consumes less than 50 Watt (W) of electrical power. In an embodiment, the radiation source 10 may consume less than 40 W, 30 W, 25 W, 20 W, 15 W, 10 W or 5 W of electrical power. The amount of electrical power consumed by the radiation source 10 may be within a range, such as 5-50 W, 10-45 W and other ranges with endpoints described above.

The radiation source 10 may have different levels of emission power, which may have a unit of Watt (W). The radiation 100 emitted by the radiation source 10 may enable different levels of power density (power per unit area) depending on factors such as the radiation pattern of the radiation source 10 and the distance from the radiation source 10 at which the power density of the radiation 100 is measured. The power density enabled by the radiation 100 describes the amount of (optical) power distributed over a certain surface area and may have units such as Watt per meter ($W/m^2$) or Watt per centimeter ($W/cm^2$). For instance, assuming that a radiation source emits 10 W and is a point source having a uniform spherical distribution pattern. Then, the power density received at a location 2 meters away from the radiation source is $10/(4\pi*2^2)$=about 0.2 ($W/m^2$).

The emitted power of the radiation source 10 may vary over time. Thus, while it is possible that the radiation source 10 emits radiation 100 with a substantially constant amplitude (which implies a substantially constant emission power) over time, it is also possible that the radiation source 10 emits radiation 100 with other time-domain characteristics. In an embodiment, the radiation source 10 emits radiation 100 that is pulsed. A pulse may have a pulse duration and a pulse period. The pulse duration is the duration of a pulse. The pulse period designates how often a pulse repeats (which may also be described as "pulse frequency", which is the inverse of the pulse period). Note that the radiation amplitude or intensity is not necessarily zero between the pulses. Between the pulses, there could still be some amount of radiation (less than during a pulse), such as radiation induced by transients. In an embodiment, the threshold amplitude or intensity that defines a pulse is an amount that is sufficient to induce PBM effects in a living organism, such as a human body.

The shape of the pulse is not particularly limited. In an embodiment, the pulse may have a rectangular shape. Other shapes are also possible, such as sinusoids, triangles and sawtooth. A combination of pulses with different shapes are also possible. In an embodiment, the end of a pulse may be defined as the point where the amplitude drops below a predetermined threshold. The predetermined threshold may be about zero or non-zero. The predetermined threshold may be defined in relative terms, such as a percentage of the peak amplitude, such as 0.001%, 0.01%, 0.1%, 1%, etc. The predetermined threshold may also be defined in absolute terms. Some pulse shapes may particularly suit certain conditions that depend on the radiation source, such as the delay or decay effects related to the materials used as the radiation source (e.g., semiconductor or phosphor). A rectangular pulse shape may be advantageous because of the wide variety of available generators for such pulses, such as integrated circuits. A sinusoidal pulse shape may be beneficial where spreading out the radiated power is needed.

In an embodiment, the radiation 100 emitted is pulsed and may have a pulse duration in the range of about 0.05-500 ms. In an embodiment, the pulse duration may be in the ranges of about 0.1-100 ms or about 0.5-20 ms or about 1-20 ms or about 4-10 ms. Other ranges for the pulse duration, such as 1-40 ms, 4-40 ms and 8-30 ms, are also possible. Depending on the types of PBM responses desired to be induced, other values or ranges of the pulse duration are also possible, such as 5 ms, 13.4 ms, 27.78 ms; 16 ms, 8 ms and 4 ms each having a respective pulse frequency of 50 Hz, 100 Hz and 200 Hz; and 8 ms and 40 ms. These values and ranges may be particularly suitable for achieving certain types of medical benefits.

In an embodiment, the radiation 100 emitted is pulsed and may have a pulse frequency (inverse of pulse period) in the range of about 0.01-10000 Hz. In an embodiment, the pulse frequency may be in the ranges of about 0.1-2500 Hz or about 1-160 Hz. Other ranges for the pulse frequency are also possible.

A parameter related to pulse duration and pulse period (frequency) is duty cycle. The duty cycle describes the ratio between the period of a pulse and the period between pulses, and is usually expressed as a percentage. The duty cycle may be defined as the pulse duration divided by the pulse period. In an embodiment, the radiation 100 has a duty cycle of not greater than 50%. Other maximum duty cycle values are also possible, such as 40%, 30%, 20%, 10%, 5%, 3%, 2%, 1%, 0.5%, 0.1%, 0.05% and 0.01%. In an embodiment, more than one duty cycles may be used; they may also be used alternatingly. Variable duty cycles directly allow different dosage over different times, especially if combined with variable frequencies. For certain types of radiation sources whose driving strength are related to the duty cycle (because of, e.g., thermal constraints), variable duty cycles may additionally allow different power densities over different time by providing different cooling periods.

Pulsed radiation 100 may have a peak emission power. In an embodiment, a peak emission power of the radiation emitted by the radiation source (through, e.g., a pulsed driving current) is at least 25 W. In an embodiment, the peak emission power may be at least 50 W, 75 W, 100 W, 150 W, 200 W, 300 W, 400 W or 500 W. Constraints to the peak emission power include the available electrical power and the number and physical capabilities of the devices used in the radiation source 10. In an embodiment, a peak emission power of the radiation 100 emitted by the radiation source 10 is sufficient to induce beneficial photo-biomodulation (PBM) response in a human body.

If the radiation 100 emitted by the radiation source 10 is pulsed, then the power density of the radiation 100 measured at a distance away from the radiation source 10 may also vary over time and thus may have peaks and valleys. In other words, if the power density is measured over time and displayed on, e.g., an oscilloscope, then a pulsed signal could be displayed. In an embodiment, the achieved peak power density enabled by the radiation 100 emitted by the radiation source 10 is 0.4-50 mW/cm$^2$ and optionally 1-50 mW/cm$^2$ and optionally 5-15 mW/cm$^2$, although other suitable ranges are also possible. The (peak) power density may be measured at a common average distance of between about 0.2 and about 5 m from the radiation source 10, depending on the usage scenario. Preferably, the radiation source 10 may enable the aforementioned ranges of power density at a common average distance of between about 0.5 and 3 m from the radiation source 10. In another embodiment, the (peak) power density may be measured at a distance where the illuminance of the lighting arrangement 1a is about 500 Lux (lx).

It is well-known that power multiplied by time results in energy. Therefore, the amount of radiation may also be expressed in energy (e.g., Joule (J)) or energy density (e.g., J/cm$^2$). In an embodiment, the radiation source 100 emits at least 3,000 Joule in the pre-determined spectrum within 8 hours (other energy values and duration values, such as 1, 2, 4 and 6 hours, are also possible).

The total amount of radiation energy received at a given point over a certain period may be expressed in energy per unit area. This amount may be referred to as "fluence" or simply "dose" or "dosage", with J/cm$^2$ being an exemplary unit.

In an embodiment, the radiation source 100 may be configured to deliver a dosage that is sufficient to induce PBM response in a human body. Different dosages may be required depending on the type of the PBM response to be induced. In an embodiment, the radiation source 100 may be configured to deliver a dosage of 0.01-5 J/cm$^2$ measured at a common average distance from the radiation source. The common average distance from the radiation source may be between about 0.2 and about 5 m, depending on the usage scenario. Preferably, the dosage may be measured at a common average distance from the radiation source may be between about 0.5 and 3 m. In another embodiment, the delivered dosage may be measured at a distance where the illuminance of the lighting arrangement 1a is about 500 Lux (lx).

The light source 11 is adapted to emit visible light. The light source 11 emits visible light 110 upon receiving or being energized by a driving signal. The driving signal may be an electric signal. In an embodiment, the driving signal is an electric current, such as a second driving current 111. The light source 11 may be used for any of general lighting, task lighting and accent lighting purposes. In some embodiments, the emitted visible light 110 may have a color point that has a distance less than 10 SDCM to a black body line in a CIE XYZ color space. In some embodiments, the color point may have a distance within 8 SDCM, 7 SDCM, 6 SDCM, 5 SDCM or 3 SDCM from the black body line. Such kinds of light may be useful for general lighting, task lighting and accent lighting purposes.

In the context of this document, "general lighting" (which may sometimes be referred to as "general illumination") means that it is not special-purpose illumination (e.g., killing bacteria, growing plants, detecting cracks, medical treatment, tanning) other than just illuminating to assist human vision. It means that when a space is too dark for people to work/live in, and its illumination level must be raised, the embodiments of this document can be used for the purpose of increasing the illumination level of that space such that it is convenient for people to live and work in that space.

In the context of this document, "task lighting" refers to a form of general lighting with more specific applications, such as for sport fields, hospitals, open streets and motorways. Compared to general lighting, task lighting may require higher output to achieve a higher brightness and/or cover a larger area. In the context of this document, "accent lighting" refers to a form lighting that is intended to produce a visual accent, with common applications including accentuating houseplants, sculptures, painting and other decorations, and emphasizing architectural textures or outdoor landscaping.

The color of a light may be described as a point in a color space, such as a CIE XYZ color space. The color of visible light 110 for general lighting purposes is not limited to strictly white light, which occupies a very small area, if not a single point, in the color space. Exemplary colors points that may considered suitable for general, task or accent lighting purposes include the blackbody line, a portion of the blackbody line, and colors points within certain distances from (a portion of) the blackbody line.

The blackbody line is a collection of the color points in a CIE color space of electromagnetic radiation emitted by a blackbody at various blackbody temperatures. Different blackbody temperatures lead to different hues. For example, an incandescent lamp may emit light at 2700K, which demonstrates a light red or orange hue that is often called a "warm" white light. The hue at higher temperatures, such as 4000K and 6500K, is whiter and sometimes called "cooler".

Color points suitable for general, task or accent lighting purposes are not limited to those on the blackbody line and may include those within certain distances from the blackbody line. This may be the case for non-blackbody-radiation light sources, such as fluorescence lamps and LEDs.

Figure 1B:
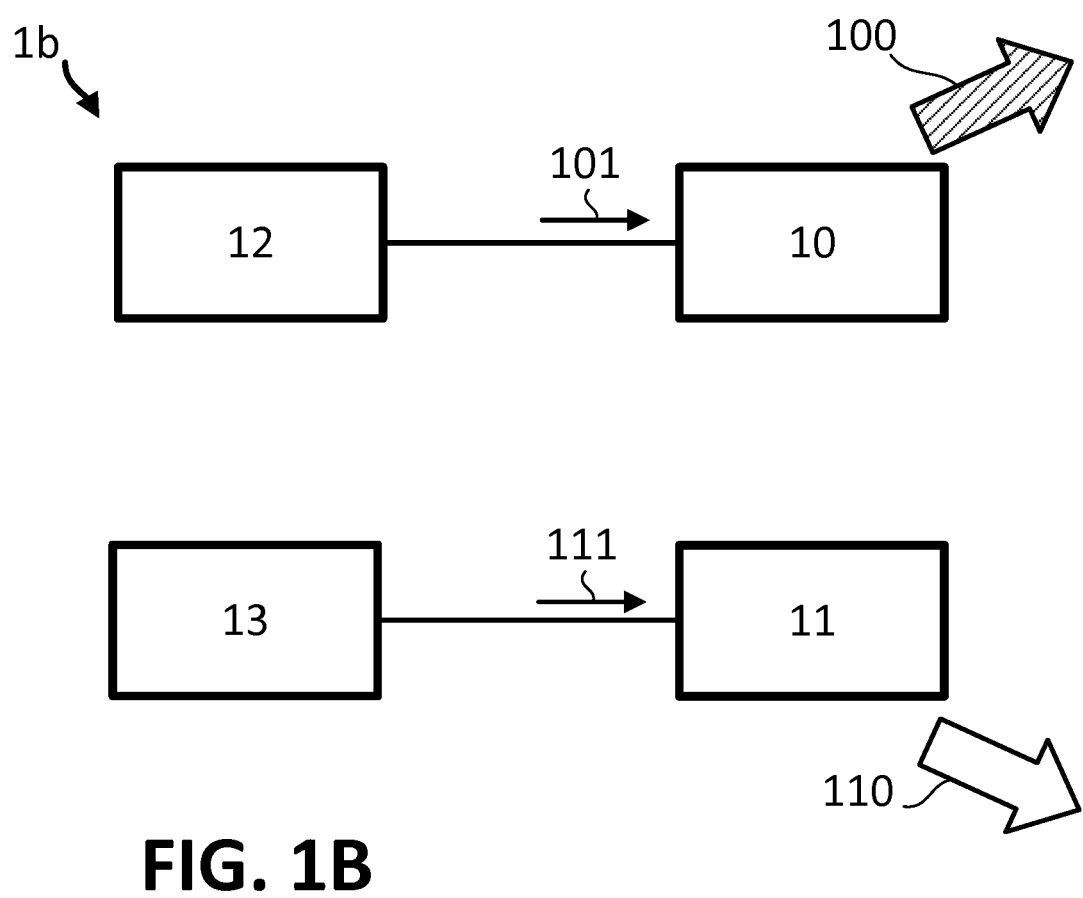
FIG. 1B schematically shows a lighting arrangement in accordance with an embodiment of the present disclosure.
Figure 1C:
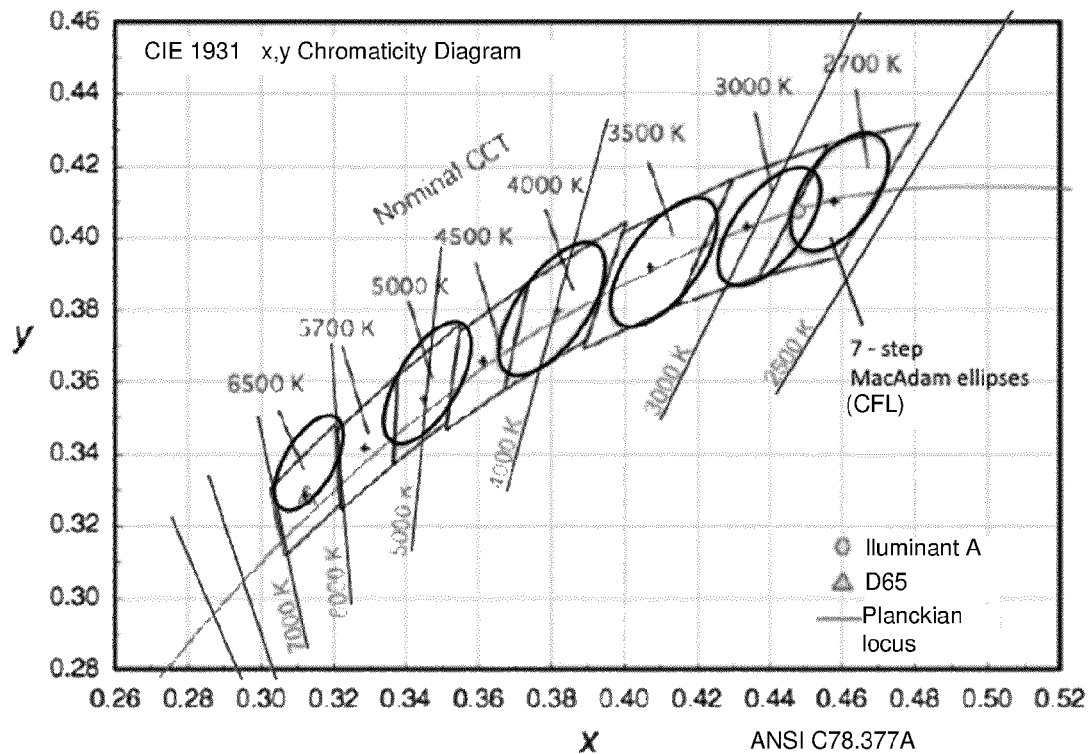
FIG. 1C illustrates a part of the CIE XYZ color space that includes a portion of the blackbody line.

FIG. 1C illustrates a part of the CIE XYZ color space from the ANSI C78.377-2008 standard. The illustrated color space includes a portion of the blackbody line, labeled as "Planckian locus". The six ellipses, called 7-step MacAdam ellipses, respectively indicate the boundary of areas within 7 SDCM from the color points corresponding to 2700K, 3000K, 3500K, 4000K, 5000K and 6000K on the blackbody line. Persons ordinarily skilled in the art understand that SDCM has the same meaning as a MacAdam ellipse. Visible light with a color point within 7 SDCM from a point on the blackbody line, preferably from a point between 1700K and 6500K, may still be considered by naked human eye as relatively white and may be suitable for general, task or accent lighting purposes.

Figure 1D:
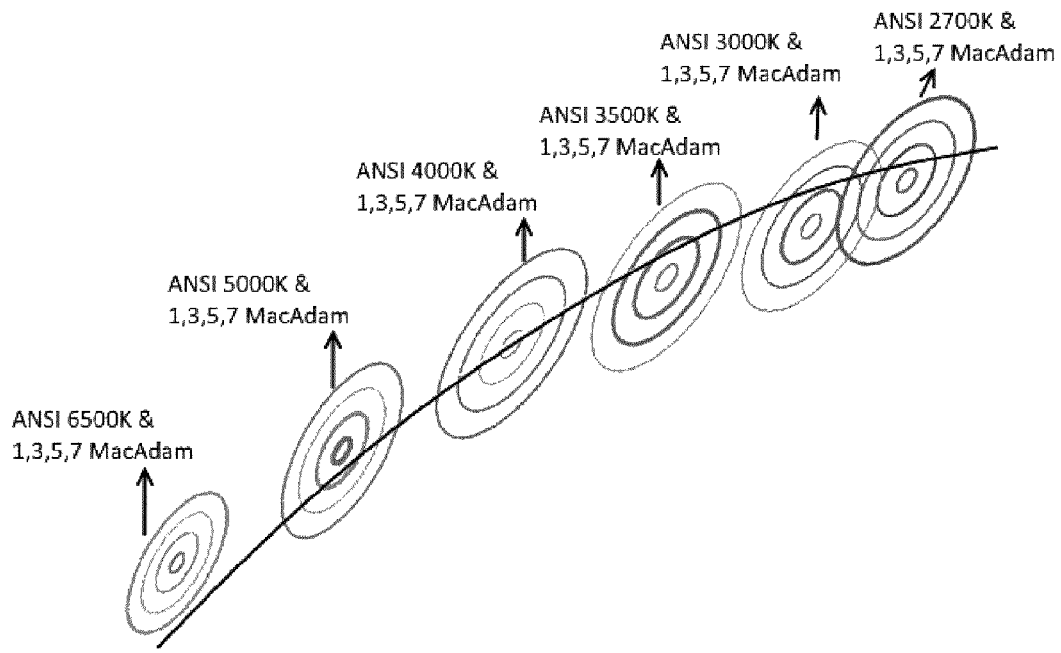
FIG. 1D illustrates a portion of the blackbody line with MacAdam ellipses around a certain number of color points along the blackbody line.

FIG. 1D illustrates a part of the blackbody line in the CIE XYZ color space with four MacAdam ellipses around each of the color points corresponding to 2700K, 3000K, 3500K, 4000K, 5000K and 6000K. The four MacAdam ellipses respective indicate 7 SDCM, 5 SDCM, 3 SDCM and 1 SDCM from the corresponding color temperature. Visible light with a color point within any of the illustrated MacAdam ellipse may be suitable for general, task or accent lighting purposes.

Figure 1E:
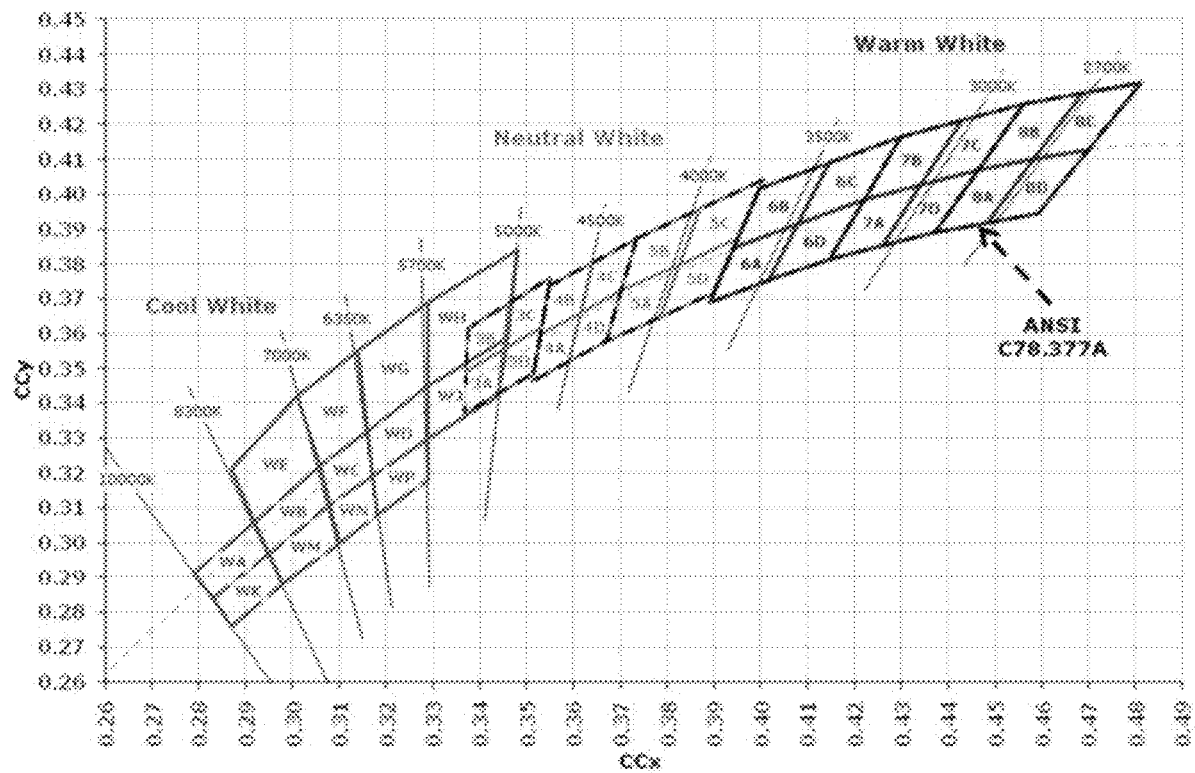
FIG. 1E illustrates segmenting the bins shown FIG. 1C.

Refer back to FIG. 1C. Another way of indicating color points that may be suitable for general, task or accent lighting purposes is through binning, such as the ANSI C78.377-2008 binning standard indicated in FIG. 1C as various quadrilaterals. The binning shown in FIG. 1C is not exhaustive. For example, FIG. 1E illustrates segmenting the bins shown FIG. 1C that could allow a more precise specification.

In an embodiment, the light source 11 (or the lighting arrangement 1a comprising the light source 11) may be adapted to generate visible light 110 having a luminous flux which does not fluctuate by more than 20% or 15% or 10% or 5% or 3% when the light source 11 is in use. Visible light 110 with a limited fluctuation in the luminous flux has less flicker and thus is more suitable for general lighting. In an embodiment, the light source 11 (or the lighting arrangement 1a comprising the light source 11) may be adapted to generate visible light without perceptible flicker to the human eye, e.g., very low amounts of flicker or only flicker at frequencies too high for a human eye to perceive.

In an embodiment, the light source 11 may emit at least 25 lumens, which is equivalent to about two candles. Such a light source may be useful for home decoration purposes. In an embodiment, the light source 11 may emit at least 100 lumens. In an embodiment, the light source 11 may emit at least 300 lumens, which is suitable for general lighting purposes in a home. Other amounts of luminous flux are also possible to suit, e.g., general lighting in an office or a factory environment.

In an embodiment, the correlated color temperature (CCT) of the light source 11 emitting visible light 110 is in the range of about 1700-6500K, optionally in the range of about 2400-5500K, optionally in the range of about 4000-5500K. In an embodiment, the color rendering index of the light source 11 emitting visible light 110 is in the range 80-99 at a correlated color temperature of about 2700K. Such light sources may be more acceptable for general lighting purposes by a human user than, say, a single-color R, G or B light source. Needless to say, many suitable combinations of the lumens specification, the CCT and the CRI are possible.

The light source 11 may consume electrical power. In an embodiment, the light source 11 may consume an electric power of less than 120 W, optionally less than 80 W, optionally less than 30 W, depending on the power requirements of the usage scenarios for the lighting arrangement 1a.

Many sources for general lighting may be used as the light source 11. In an embodiment, the light source 11 may comprise an incandescent bulb, a halogen bulb or a fluorescence tube. In an embodiment, the light source 11 may comprise a solid-state device. In an embodiment, the light source 11 may comprise a light-emitting diode (LED), or more than one LED. The types of LED are not particularly limited.

The radiation source 10 and the light source 11 may each consume electrical power. In an embodiment, the radiation source 10 may consume a fraction of the electrical power consumed by the light source 11 when the lighting arrangement 1a is in use. The fraction may be not greater than 50%, optionally not greater than 25%, optionally not greater than 10%, optionally not greater than 5%. A lower fraction means that the user of the lighting arrangement 1a may obtain the additional benefit of PBM-inducing radiation at a lower marginal power consumption in addition to the benefit of general lighting provided by the light source 11. The amount of electrical power consumed by the radiation source 10 may also be expressed in terms of the fraction of the total electrical power consumption of the radiation source 10 and the light source 11 combined, for example, less than two-thirds, less than one-fifths or in a range of about 5%-10%.

The driver circuit 12 may provide driving signals to drive or energize the radiation source 10 and the light source 11.

In an embodiment, the driver circuit 12 may provide the first driving current 101 to the radiation source 10 and the second driving current 111 to the light source 11. The first driving current 101 and the second driving current 111 may differ from each other. In an embodiment, the driver circuit 12 may provide the first driving current 101 to the radiation source 10 and not to the light source 11; and/or the driver circuit 12 may provide the second driving current 111 to the light source 11 and not to the radiation source 10.

In an embodiment, the first driving current 101 may be pulsed and have a duty cycle of less than 20%, optionally less than 10%, optionally less than 5%. In an embodiment, the pulsed first driving current 101 is not provided to the light source 11.

In an embodiment, the radiation source 10 may be such that it reacts almost instantly (i.e., with no or a negligible amount of delay) to the first driving current 101, in which case how the first driving current 101 varies over time and how the radiation 100 emitted by the radiation source 10 varies over time are similar or substantially identical to each other. For example, if modern solid-state radiation device(s) (such as LED), which can react rapidly to the driving current, are used as the radiation source 10 and driven by a pulsed driving current 101, then the radiation 100 emitted by the radiation source 10 is also pulsed with similar pulse parameters (such peak intensity, pulse duration, pulse period/frequency, duty cycle, etc.).

In an embodiment, the second driving current 111 driving the light source 11 may also be pulsed. An example is using pulse-width modulation to achieve dimming control in LED general lighting devices. In an embodiment, the second driving current 111 may be DC or AC, which may be required by particular light sources. In an embodiment, the second driving current 111 may drive the light source 11 in a continuous-wave (CW) mode.

The optional sensor 14 may provide an input 141 to the driver circuit 12. The driver circuit 12 may modify the first driving current 101 in response to the input 141. For example, the sensor 14 may be an awareness sensor or distance sensor that instructs the driver circuit 12 to turn on or off the first driving current 101 depending on the presence and/or distance of the user. In some embodiments, what is coupled to the driver circuit 12 is not a "sensor" in a strict sense but a more generic information source that may or may not exist within the lighting arrangement 1a. For example, the input 141 may be weather or user data coming from the user's smart mobile device.

It is to be noted that the lighting arrangement 1a may include circuit blocks/elements not explicitly drawn in FIG. 1A, such as external power sources, switches, ballasts and ground pins. There may also be additional circuit blocks/elements between the radiation source 10 and the driver circuit 12 and/or between the light source 11 and the driver circuit 12 to achieve various purposes, such as controlling the first driving current 101 and the second driving current 111.

FIG. 1B illustrates a lighting arrangement 1b in accordance with an embodiment of the present disclosure. Compared to the lighting arrangement 1a, the lighting arrangement 1b additionally comprises a driver circuit 13. The driver circuit 13 is optional. The addition of the driver circuit 13 may provide more flexibility in driving the light source 11. For example, the light source 11 may be easily driven in a manner different from the radiation source 10. Moreover, separating the driver circuits for energizing the light source 11 and the radiation source 10 may help reduce interference and cross-talk.

FIGS. 2A-2D schematically present different embodiments incorporating the above-discussed lighting arrangements in accordance with the present disclosure.

Figure 2A:
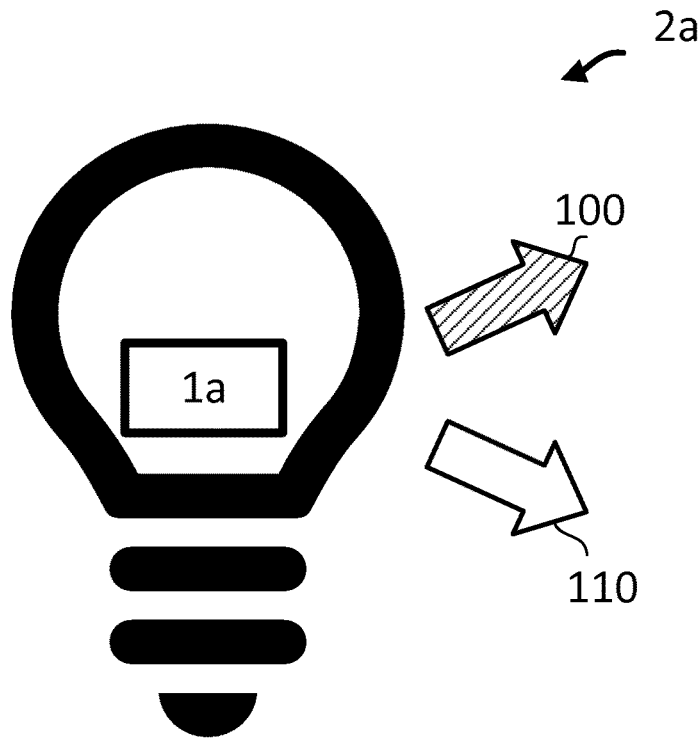
FIG. 2A illustrates a bulb in accordance with an embodiment of the present disclosure.

FIG. 2A illustrates a bulb 2a comprising a lighting arrangement 1a. The bulb 2a may be a retrofit bulb that a general consumer would find familiar and easy to use. The light source 11 in the lighting arrangement 1a may provide sufficient visible light 110 to make the bulb 2a suitable for general lighting purpose. The visible light 110 may be sufficient in both the senses of quantity (e.g., enough brightness) and quality (e.g., no flicker, comfortable color, etc.). After installing and turning on the bulb 2a, the user not only receives visible light 110 for illumination but is also exposed to the radiation 100 that may induce beneficial PBM response in the human body. That is, the bulb 2a according to an embodiment of the present disclosure achieves two functions, making it far more useful than a traditional light bulb.

Figure 2B:
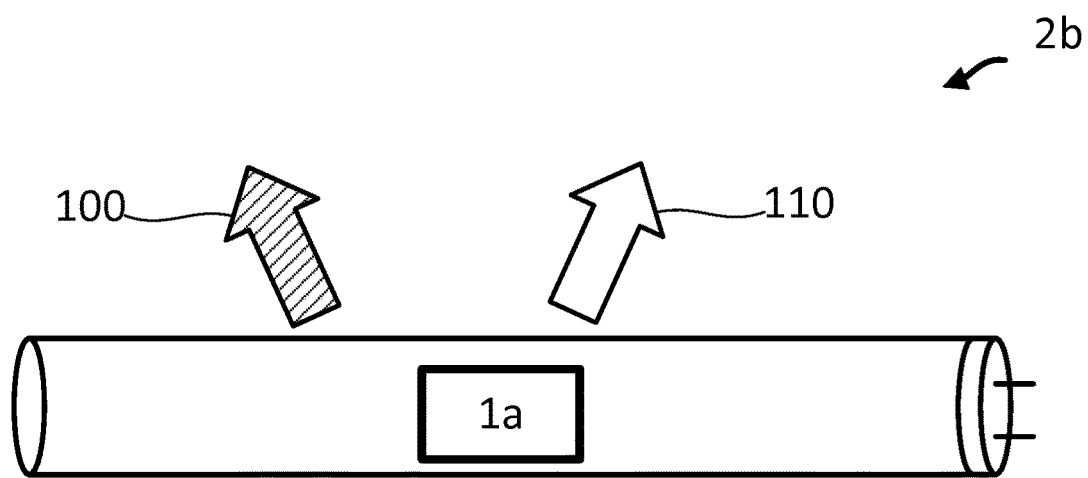
FIG. 2B illustrates a light tube in accordance with an embodiment of the present disclosure.

FIG. 2B illustrates a light tube 2b comprising a lighting arrangement 1a. The light tube 2b may be a retrofit light tube that a general consumer would find familiar and as easy to use as a traditional fluorescent tube. The light tube 2b may be adapted to fit in a standard fluorescent luminaire. Similar to the bulb 2a, the light tube 2b may provide dual functions (general illumination and health benefits) to its user.

Figure 2C:
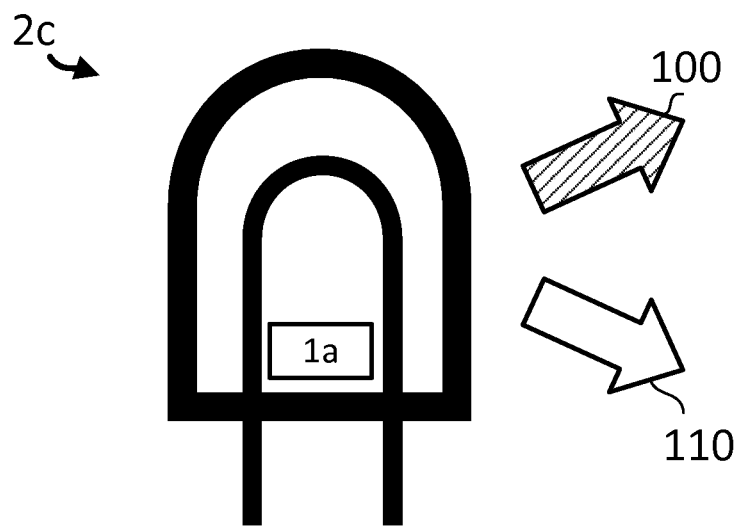
FIG. 2C illustrates a lamp in accordance with an embodiment of the present disclosure.

FIG. 2C illustrates a lamp 2c comprising a lighting arrangement 1a. The lamp 2c may be an off-the-shelf lamp that is adapted to easily fit with existing standard fitting. A general consumer can buy a lamp 2c and use it without the need to call an electrician to adapt the standard fitting, at the same time providing the great versatility and benefits as the lighting arrangement 1a to the user. In an embodiment, the lamp 2c may be customized to fit with a specific fitting.

Figure 2D:
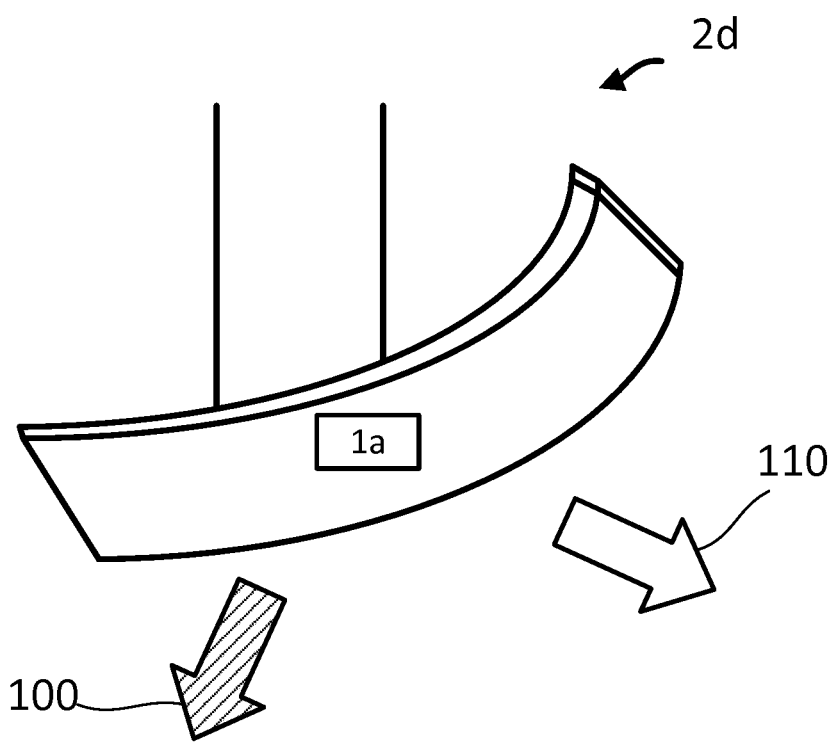
FIG. 2D illustrates a luminaire in accordance with an embodiment of the present disclosure.

FIG. 2D illustrates a luminaire 2d comprising a lighting arrangement 1a. The luminaire 2d may comprise a light fitting to accommodate the lighting arrangement 1a or a lamp comprising the lighting arrangement 1a and may optionally comprise decorative elements, such as shades, base and/or housing. The luminaire 2d may be used, e.g., in a household or an office environment and may comprise additional light sources to satisfy additional lighting requirements. In an embodiment, the luminaire 2d may be available as off-the-shelf products with all elements of the lighting arrangement 1a already mounted in the luminaire 2d. The user can buy such a luminaire 2d, provide it with electrical power, and directly enjoy the dual benefits of general illumination and medical benefits.

Some elements of the lighting arrangement 1a may be mounted externally to the luminaire 2d. For example, the radiation source 10 and the light source 11 may be mounted within the luminaire 2d while the driver circuit 12 is placed outside but connected to the luminaire 2d. If the radiation source 10 and the light source 11 are driven by two driving circuits, one of the driving circuits may be mounted within the luminaire 2d and the other may be placed outside the luminaire 2d. It is also possible to use more than one luminaires with some elements of the lighting arrangement 1a mounted in one luminaire and the other elements of the lighting arrangement 1a mounted in another luminaire. For example, the radiation source 10 and the driver circuit 12 may be mounted on one luminaire, and the light source 11 and the driver circuit 13 may be mounted on another luminaire. It is also possible to mount the radiation source 10 on one luminaire and the light source 11 on another luminaire and make the driver circuit 12 mounted outside of yet connected to both luminaires.

Although the lighting arrangement 1a is illustrated in FIGS. 2A-2D, it should be evident that this is not limiting.

Figure 3:
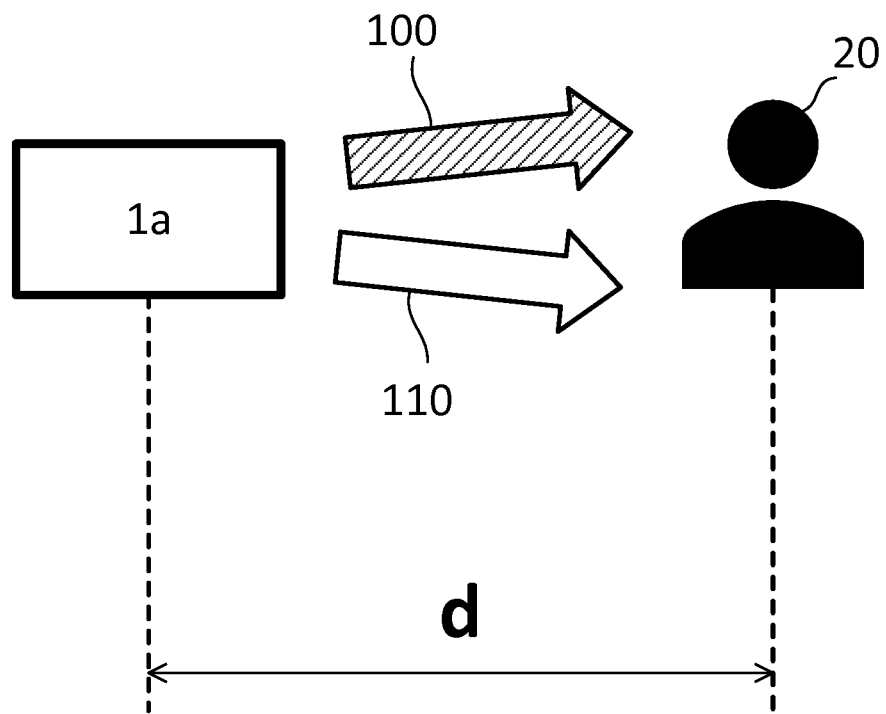
FIG. 3 illustrates a usage scenario of a lighting arrangement accordance with an embodiment of the present disclosure.

FIG. 3 illustrates a usage scenario of the lighting arrangement 1a in accordance with an embodiment of the present disclosure.

In FIG. 3, the lighting arrangement 1a emits the radiation 100 and the visible light 110. A user 20 is a distance d away from the lighting arrangement 1a. The distance d may be, for example, 1 meter. The visible light 110 illuminates the surroundings of the user 20. The user 20 is exposed to the radiation 100. The power density enabled by (or resulting from) the radiation 100 that the user 20 is exposed to depends on factors such as the distance d and the radiation pattern.

As a non-limiting example, assume that the radiation source 10 has an optical emission power of 500 W with a peak wavelength of 850 nm light in order to enable a power density of 8 mW/cm$^2$ at a 2 m distance from the radiation source 10. If the radiation source 10 is operated in the CW mode (i.e., non-pulsed, substantially constant emission at 500 W), then the required amount of electrical power is 1000 W assuming an electric-to-optical-power-conversion efficiency of 50%.

In the above non-limiting example, the user 20 at a 2 m distance could be exposed to a power density of 8 mW/cm$^2$, sufficient to induce PBM response. The dosage (energy density) that the user 20 receives is 8 mW/cm$^2$ multiplied by the exposure time.

The radiation source 10 in the above non-limiting example may be operated or driven in a different manner that provides additional benefits, as explained below.

Figure 4:
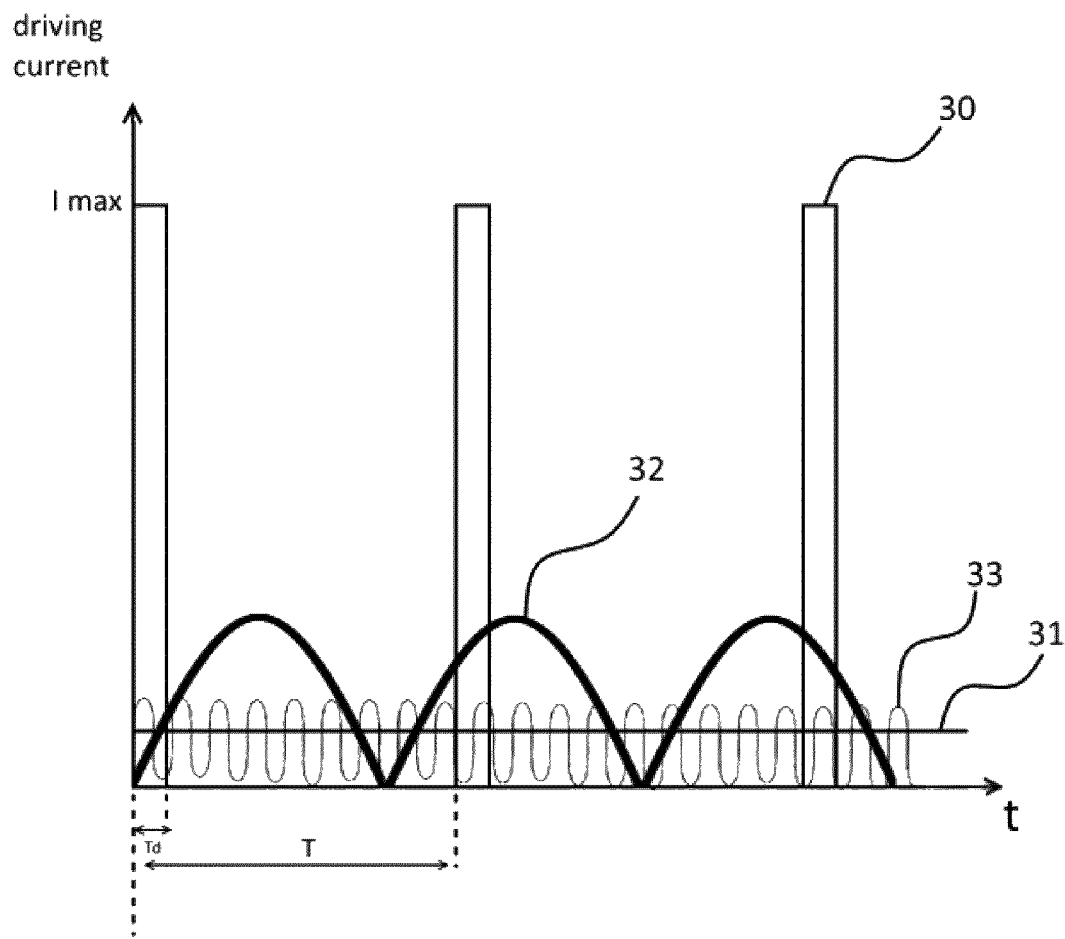
FIG. 4 illustrates a graph of driving currents over time in a lighting arrangement in accordance with an embodiment of the present disclosure.

Refer to FIG. 4, which illustrates a graph of various driving currents over time in a lighting arrangement in accordance with an embodiment of the present disclosure. Curve 30 represents the first driving current 101, and curve 31 represents the second driving current 111. As illustrated, the first driving current 101 represented as curve 30 is pulsed, while the second driving current 111 represented as curve 31 is not. The non-pulsed second driving current 111 may help the light source 11 to provide stable visible light suitable for general lighting. However, the second driving current 111 may have different shapes, some examples being illustrated by curves 31-33. For example, the second driving current 111 may be a steady DC current, as exemplified by the curve 31. As another example, the second driving current 111 may be a rectified AC current, as exemplified by the curve 32. The rectified AC current may have a frequency of, e.g., 100 or 120 Hz; such driving current may be suitable for visible light sources such as an incandescent lamp. As another example, the second driving current 111 may be pulsed, as exemplified by the curve 33. The curve 33 may represent a pulse-width modulated (PWM) driving current having a pulse frequency in the range about 20000 Hz-300000 Hz, optionally about 50000 Hz-300000 Hz. Pulsing the light source 11 at an appropriate frequency may provide dimming control without generating flickers perceptible by the human eye. It is evident that the scale in FIG. 4 is only for illustration and not exact.

As shown in FIG. 4, the first driving current 101 has a pulse duration of $T_d$ and a pulse period T. The duty cycle is $T_d$ divided by T. During the pulse, the radiation source 10 is operated at maximum emission; in between the pulses, the radiation source 10 is turned off.

As a non-limiting example, assume that the pulse duration of $T_d$ is 2 ms and the pulse period is 1 s (i.e., a pulse frequency of 1 Hz), namely a duty cycle of 0.2%. The so-driven radiation source 10 would still deliver a power density of 8 mW/cm$^2$ at a 2 m distance during the pulse, but the average optical power in the pulsed mode becomes 1 W instead of 500 W because the radiation is present during 0.2% of the time. This would also imply a reduction of electrical power consumption by the same factor of 500.

That is, the same amount of emission power (at the source) and power density (at a distance from the source) can be achieved by pulsing with a corresponding decrease in electrical power consumption, often by a large factor. Since apparatuses for general lighting typically have limits on electrical power consumption, pulsing the radiation source 10 may maintain the PBM response-inducing level of power density at a stricter electrical power budget. Another consequence of pulsing the radiation source 10 is that the radiation dosage (related to energy density) received by the user 20 within the same amount of time would decrease by the corresponding factor. However, a lower dosage could actually be a benefit as it decreases the risk of over-dosage. That is, the user 20 would not be worried about when to turn off the lighting arrangement 1a and simply use it as a conventional general lighting source.

Figure 5:
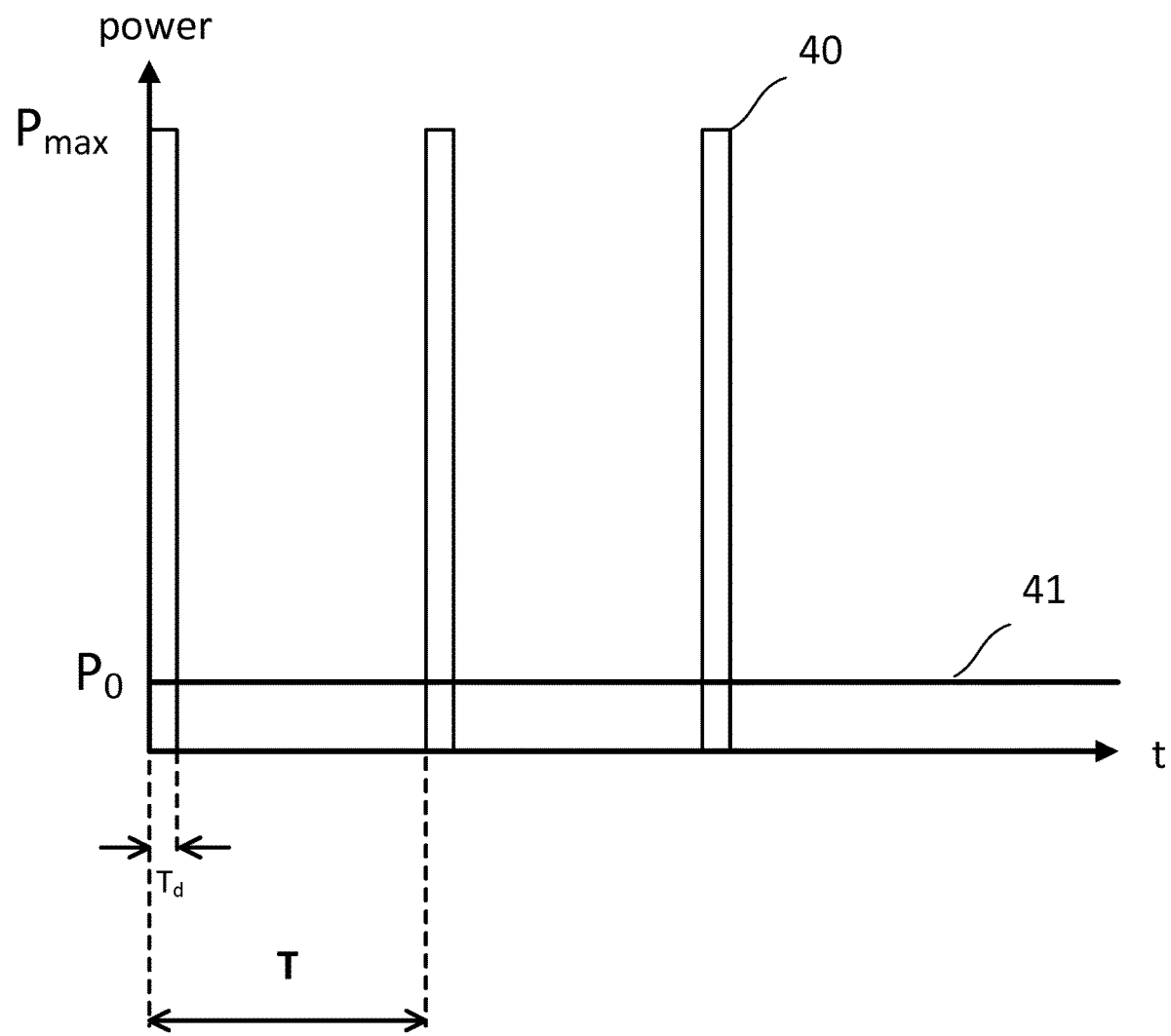
FIG. 5, which illustrates a graph of emission power over time from lighting arrangement in accordance with an embodiment of the present disclosure.

Refer to FIG. 5, which illustrates a graph of emission power over time of the radiation source 10 and the light source 11 of a lighting arrangement in accordance with an embodiment of the present disclosure. Curve 40 represents the radiation 100, and curve 41 represents the visible light 110. If the radiation source 10 and the light source 11 can react instantly to the respective driving signals, then the shape of the radiation 100/visible light 110 would match the respective driving signals; if not, delays and transients may occur. For example, the intensity of light emitted by a thermal emitter such as an incandescent bulb driven by a rectified AC current would change more slowly than the rectified AC current because of thermal inertia. As another example, driving an LED with a PWM signal in a sufficiently high frequency range suitable for dimming control may create light that looks substantially constant to the human eye. The inventive concept behind the embodiments, however, would stay substantially identical.

Depending on the type of the radiation sources used and the amount of PBM-inducing radiation required, the magnitude of the first driving current, the pulse duration, the pulse period and the duty cycle may change.

Figure 6A:
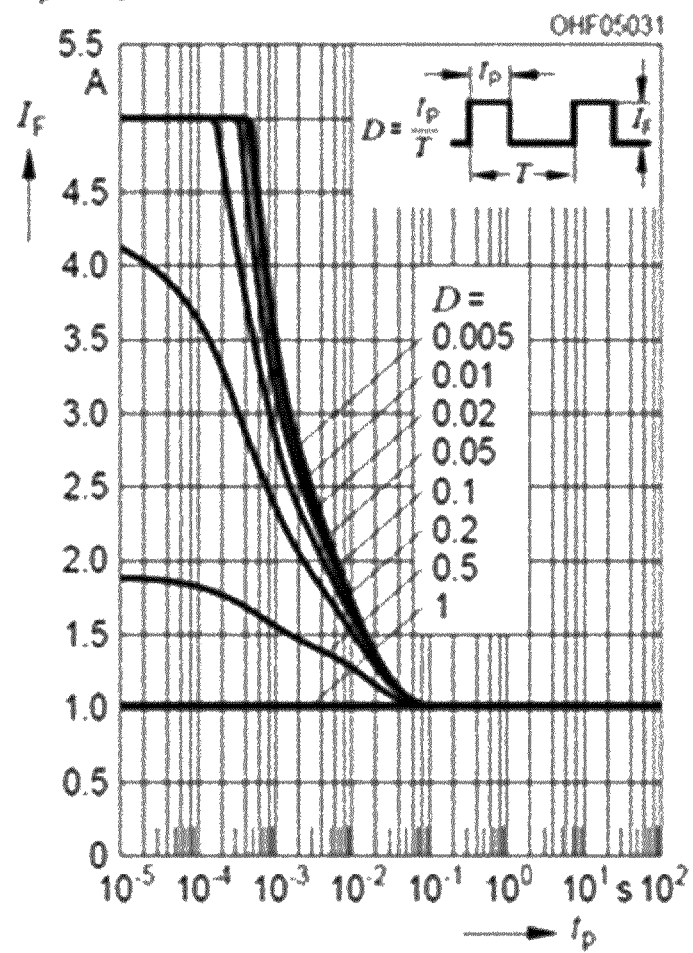
FIG. 6A illustrates the permissible pulse handling capability of a radiation source suitable for being used in embodiments of the present disclosure.

Refer to FIG. 6A, which illustrates, for a common type of high power SSL radiation source with a centroid wavelength of 850 nm, the amount of permissible driving current (along the vertical axis) under different conditions of pulse duration (along the horizontal axis) and duty cycle (represented by the family of curves).

It is known that several types of radiation sources have thermal constraints that limit their permissible driving current. The light emitting diode is an example: an excessive amount of forward current could raise the junction temperature so high that it reduces radiation output and thus efficiency. However, pulsing in combination with a selected amount of duty cycle allows the radiation source to cool down between the pulses, thereby allowing an enhanced permissible driving current. This can be seen in FIG. 6A, which relates to the pulsing handling capability of an LED: if the radiation source is not pulsed (D=1), then the driving current is at most 1 A; if the radiation source is pulsed with a duty cycle of 20% (D=0.2) and a pulse duration of 0.1 ms, then the driving current can exceed 3.5 A. In other words, pulsing can enable an enhanced permissible driving current to get more radiation output from the same (number of) radiation source in a reliable manner.

Although the plot in FIG. 6A relates to a specific type of high power SSL (solid state lighting) near infrared radiation source, pulsing a radiation source to enable enhanced permissible driving currents is generally applicable to all SSL radiation sources and not limited to any specific type of SSL radiation sources.

Figure 6B:
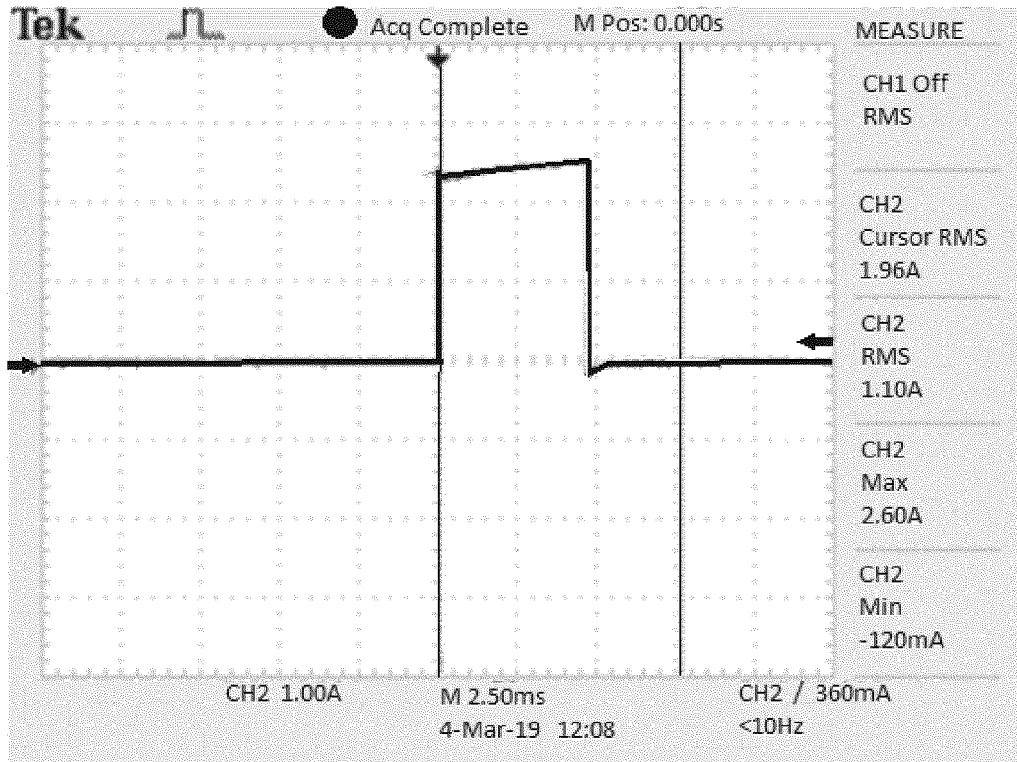
FIG. 6B shows measurement results of a driving current and the corresponding radiation, in accordance with an embodiment of the present disclosure.
Figure 6B:
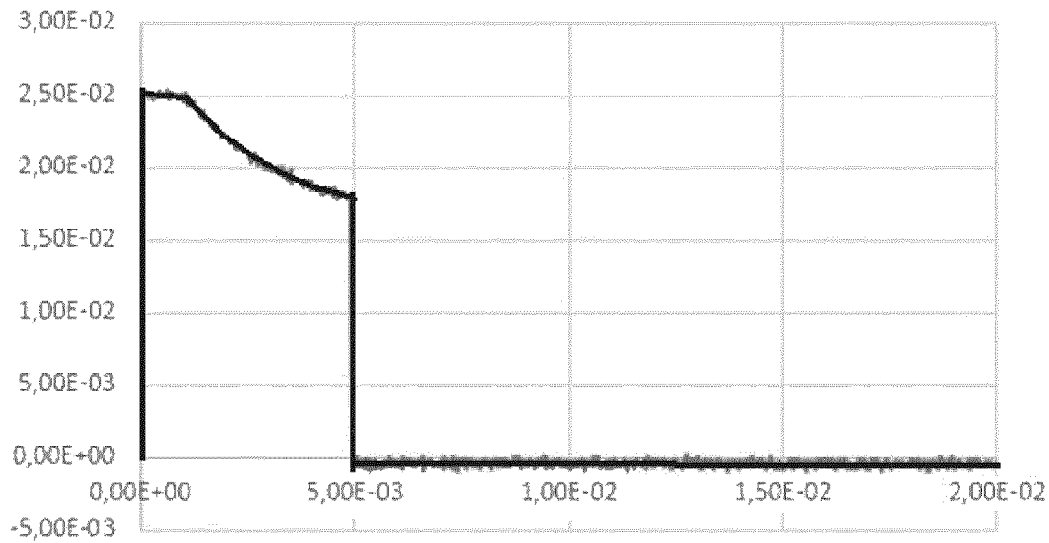

The effect of pulsing a radiation source has been experimentally verified. FIG. 6B shows the measurement results of the driving current fed into a light emitting diode different from that associated with FIG. 6A and the corresponding radiation output at 850 nm. The top part of FIG. 6B shows a driving current that averages at about 2.5 A and spans about 5 ms. The bottom part of FIG. 6B shows a measured radiation intensity that is stable for about 1 ms and then drops by about 28%. This can be explained with the pulse handling capability of the radiation source in use: a driving strength of 2.5 A is permissible if the duty cycle is less than about 20% (the measured radiation intensity starts thermal drooping at 1 ms, which is about 20% of the whole pulse) and the pulse duration of less than about 1 ms.

The ability of pulsing to permissibly drive the radiation source at different enhanced degrees may be exploited to reduce the cost of the lighting arrangement that supplies a specific amount of PBM-inducing radiation. This can also be seen in FIG. 6A: a duty cycle of 2% (D=0.02) and a pulse duration of 5 ms can enable a driving strength of about 2.2 A, whereas the same duty cycle with a longer pulse duration of 10 ms can enable a driving strength of about 1.7 A. That is, this example shows that a lighting arrangement whose radiation sources operate at a shorter pulse duration may achieve the same amount of radiation power density with a fewer number (about 20%) of the radiation sources than operating the radiation sources at a longer pulse duration, thereby reducing the cost of the lighting arrangement. This may be described as using pulses to thermally "quench" the radiation sources whose overdriving would otherwise not be possible. The overdriving may also reduce the cost of the lighting arrangement by allowing the use of, e.g., light emitting diodes with smaller die sizes (cheaper but thermally more constrained) or thermally less favorable packaging. Additionally or alternatively, pulsing and, in particular, overdriving can open the door to engineering thermal and mechanical aspects of the radiation sources (such as using flip-chip or wire-bonding and/or engineering the thermal flow between the radiation sources and the circuit board) in order to improve electrical (driving strength) and optical (radiation power density) aspects.

In short, the types of desired PBM responses to be induced determine the desired radiation power density and sometimes also the minimum pulse duration. The desired radiation power density determines the driving strength of the employed radiation source. The driving strength may be limited by thermal consideration, which may be overcome by more expensive radiation sources. Alternatively, pulsing and overdriving may improve the trade-off between driving strength and cost.

The following examples show how to apply the inventive concepts behind the above-discussed embodiments in some types of lighting apparatuses. The examples are for illustration only, non-exhaustive and not limiting.

Example—Linear Lamp

Figure 7A:
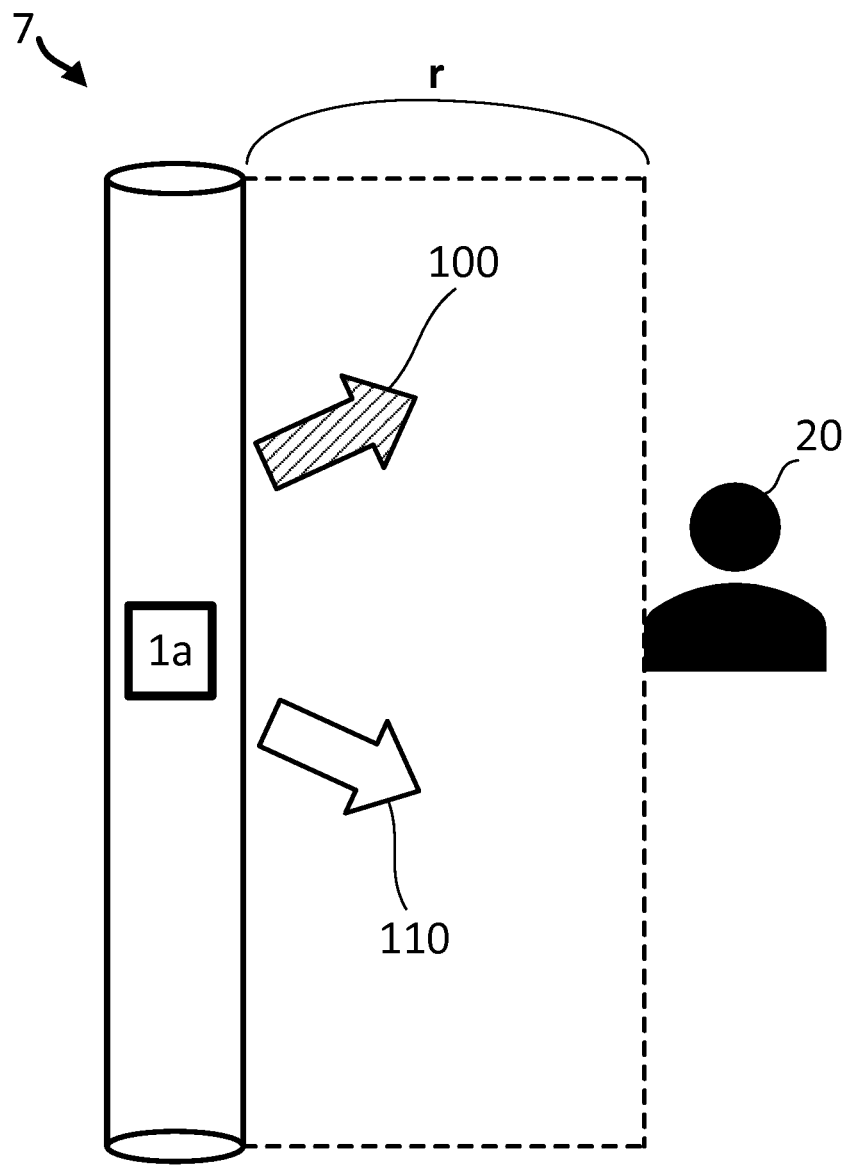
FIG. 7A conceptually illustrates a linear lamp in accordance with an embodiment of the present disclosure.

FIG. 7A conceptually illustrates a linear lamp 7 in accordance with an embodiment of the present disclosure.

The linear lamp 7 may be of T8 or T5 type for example. The linear lamp 7 may be equipped with LEDs as a replacement for fluorescent technology. The linear lamp 7 may have different lengths, such as 60 cm, 120 cm and 150 cm, e.g., designed for standard fluorescent luminaires.

In this example, assume that the linear lamp 7 is 150 cm and has a homogeneous light distribution over 180°. Assume that the linear lamp 7 comprises NIR radiation sources. At a distance r=2 m from the lamp, the surface area of a theoretical half-cylinder, which represents the theoretical light distribution at the distance of 2 m, is A=πrh=~10 m², or 1 m² per 0.1 W if the total average NIR output power is 1 W. Thus, if a user 20 is 2 meters away from the linear lamp 7, then the average power density in the NIR spectrum at the surface of the skin of the user 20 is about 10 uW/cm² (0.1 W/m²).

Assume also that the linear lamps are commonly placed in grids. Hence, the cumulative average power density on the skin of the user at 2 m average distance from the linear lamps is estimated to be on average about 60% higher, which results in about 16 uW/cm². This gain may arrive by the overlapping of the light beams, and the accumulation of diffuse light, from neighboring linear lamps placed in a certain common grid of linear lamps. The 60% value was estimated based on practical experience from installed linear lamps in real offices and may vary in reality depending on the beam pattern, the distance between the linear lamps and other factors such as the reflectivity of involved surfaces.

Medical research suggests that an average NIR power density in the range of about 1-50 mW/cm² at the skin of a human body could induce beneficial PBM responses. The inventor also recognizes that an average NIR of about 5-15 mW/cm², more particularly about 8 mW/cm², at the skin of a human body could induce particularly beneficial PBM responses, because this power density range at the skin may enable a power density of about 0.4-1 mW/cm² in a specific target layer of the skin (Dermis), which is assumed by the inventor to be most relevant for long term systemic effects. This is 500 times higher than the 16 uW/cm² that the linear lamp is capable of delivering. The 500-time difference translates into a required total average NIR output power of 500 W from the NIR radiation source in the linear lamp. This amount of NIR output power implies an electrical power consumption of more than 500 W (taking into account other factors such as non-ideal efficiency), which, although still possible to realize, may not suit certain usage scenarios such as a general lighting lamp for home use.

If the NIR radiation source is pulsed at a pulse duration of 2 ms and a pulse period of 1 s, which amounts to a duty cycle of 0.2%, then the NIR radiation source still outputs 500 W during the pulses but the average electrical power consumption over time decreases by a factor of 500 (i.e., equivalent to 1 W continuous-wave (CW)).

A possible implementation is using 200 NIR LEDs spread over 150 cm with each NIR LED having a peak output power of 2.5 W (still pulsed at 2 ms/s). Given the above optical output power and pulsing parameters, the amount of energy emitted by the radiation source after 8 hours is about 1 (W)*8 (hours)*60 (minutes/hour)*60 (seconds/minute) =28800 (J). The dose after 8 hours delivered to the skin of the user at a 2 meter distance is about 16 (uW/cm²)*8 (hours)*60 (minutes/hour)*60 (seconds/minute)=460800 (uJ/cm²)=0.4608 (J/cm²). This dosage may be suitable to induce certain beneficial PBM responses.

Assuming that the electrical-to-optical power conversion efficiency of the NIR LEDs is 50%, this implementation of the NIR radiation source consumes on average an electrical power of 2 W.

Assume that the linear lamp 7 also comprises a light source for general lighting that consumes 30 W of electrical power, which is not uncommon for household usages. Then the linear lamp 7 would consume 32 W of electrical power in total, in which 30 W is dedicated to visible light for general lighting and 2 W is dedicated to pulsed NIR radiation that may induce beneficial PBM responses. That is, the linear lamp 7 can give two benefits to its user 20: general lighting and medical benefits.

Figure 7B:
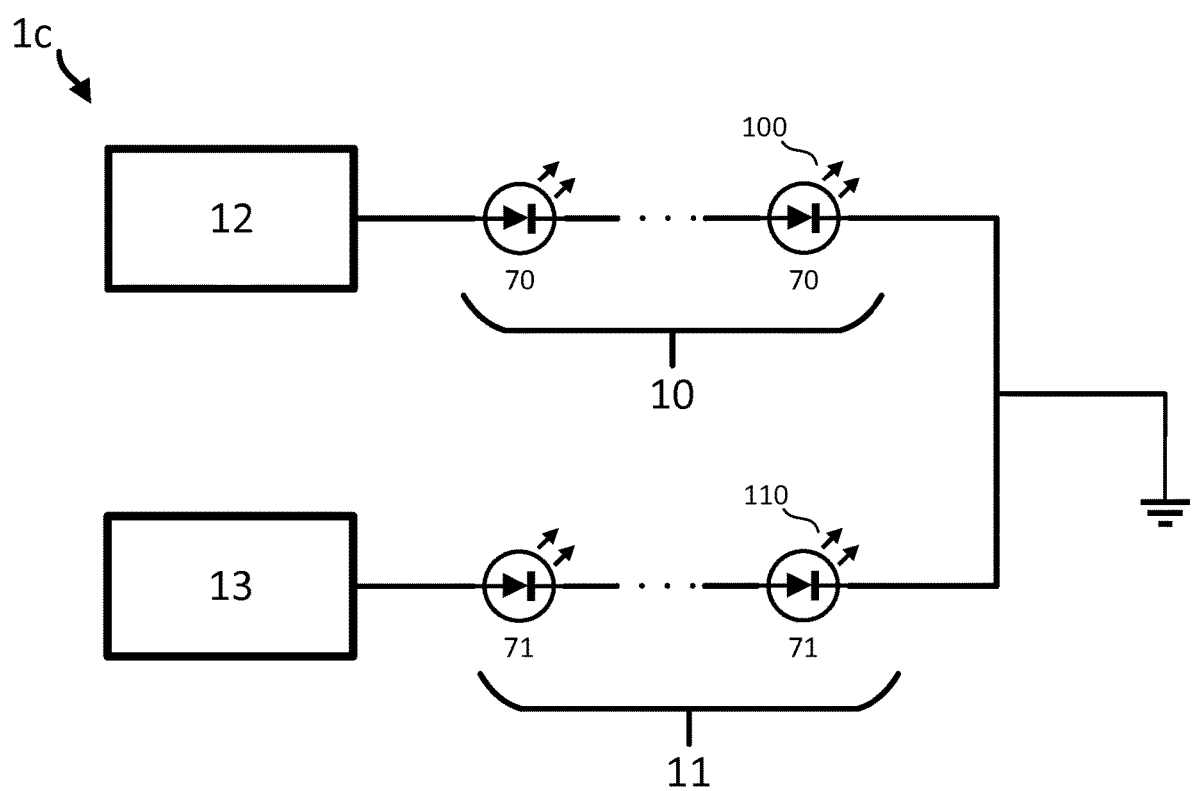
FIG. 7B schematically presents a lighting arrangement that may be used in a linear lamp in accordance with an embodiment of the present disclosure.

FIG. 7B schematically presents a lighting arrangement 1c that may be used in the linear lamp 7. The radiation source 10 may comprise a plurality of LEDs 70, the number and light properties of which may be similar to what have been described. The light source 11 may comprise a plurality of LEDs 71 providing visible light for general lighting. The driver circuit 12 may provide a pulsed driving current so that the radiation source 10 emits NIR radiation with properties described above. Another driver circuit 13 may provide a non-pulsed driving current so that the light source 11 emits visible light for general lighting.

The above examples are non-limiting, as the following variations will demonstrate.

Variation 1

To increase dosage (energy density), one may increase the pulse duration or the pulse frequency (i.e., decrease the pulse period). Increasing the pulse frequency may be favorable because some medical research results show that shorter pulses may enable a higher dose response compared to longer pulses (i.e., excitation and relaxation of ion channels). However, a higher pulse frequency and the same pulse duration requires a higher electrical power consumption.

As an example, assume that the pulse frequency is increased from 1 Hz to 10 Hz and the pulse duration stays at 2 ms. The resulting 8-hour dosage to the user would increase from 0.46 J/cm² to 4.6 J/cm². The electrical power consumption would also increase by a factor of 10, from 2 W electrical to 20 W electrical (assuming the same 50% wall-plug efficiency (WPE) of the NIR emitter).

Variation 2

In this variation, the pulse frequency increases from 1 Hz to 1.5 Hz, resulting an 8-hour dosage of 0.6912 J/cm², 50% higher than 0.4608 J/cm². In this variation, the power consumption would also increase by 50%, from 2 W electrical to 3 W electrical (assuming 50% WPE of the NIR emitter).

Variation 3

In this variation, the pulse duration decreases from 2 ms to 1 ms and the pulse frequency decrease from 1 Hz to 0.5 Hz (i.e., a 1 ms pulse is released for every 2 seconds). The power consumption then becomes 0.5 W (at 50% WPE), and the daily dose (8 h exposure) is reduced by a factor of 4 to 0.1152 J/cm².

Assume that 30 W electric power is dedicated to the light sources that emit visible light for general lighting (white-light LEDs being an example). Then the electrical power consumed by the NIR radiation source (0.5 W) is about 1.64% of the total 30.5 W. That is, the additional benefit of providing PBM-inducing NIR radiation comes only at an expense of an additional power consumption of less than 2%. The user would hardly notice such increase in his energy bills.

Variation 4

In this variation, the pulse length is 1 ms (50% of 2 ms) and the pulse frequency is 5 Hz (five times 1 Hz). The resulting electrical consumption is 5 W (at 50% WPE), and the daily dose (8 h exposure) to the skin becomes 1.152 J/cm$^2$.

Assume that 30 W electric power is dedicated to the light sources that emit visible light for general lighting (white-light LEDs being an example). Then the electrical power consumed by the NIR radiation source (5 W) is 14.29% of the total 35 W.

Variation 5

In this variation, the pulse length is 5 ms (250% of 2 ms) and the pulse frequency is 1 Hz. The resulting electrical consumption is 5 W (at 50% WPE), and the daily dose (8 h exposure) to the skin becomes 1.152 J/cm$^2$ (at the same average distance of 2 m).

Variation 6

In this variation, the radiation source comprises 100 pieces of NIR LEDs (or laser LEDs, or other solid-state lighting (SSL) sources) with a peak emission at 800 nm and 100 pieces of NIR LEDs (or laser LEDs, or other SSL sources) with a peak emission at 850 nm, instead of 200 identical NIR LEDs. The pulse parameters, amount of optical emission power and electrical power consumption stay the same.

In this variation, the total optical emission power (intensity) is enabled by two kinds of emitters having different wavelengths. This variation demonstrates that the power emitted from the lamp and also the power density and energy density delivered to the skin of the user can also be accumulated by more than one kind of NIR emission devices having different emission spectrums within the NIR light spectrum.

Variation 7

In this variation, the radiation source comprises 100 pieces of NIR LEDs (or laser LEDs, or other solid-state lighting (SSL) sources) with a peak emission at 850 nm and 100 pieces of NIR LEDs (or laser LEDs, or other SSL sources) with a peak emission at 980 nm, instead of 200 identical NIR LEDs. The pulse parameters, amount of optical emission power and electrical power consumption stay the same.

This variation again demonstrates that the power density and energy density delivered to the skin of the user can include different spectrums within the NIR light spectrum.

Variation 8

In this variation, the 200 pieces of NIR LEDs (or laser LEDs, or other SSL sources) all have a peak emission at 980 nm.

Usually, the human eye is capable of seeing light till 760-780 nm, but some humans have an extended vison of up to about 1000 nm. This variation may be useful for persons with extended vison into the NIR. Other suitable peak emission locations include 1060 nm.

Variation 9

In this variation, the radiation source in the linear lamp comprises 150 pieces of NIR LEDs (or laser LEDs, or other SSL sources) with a peak emission at 850 nm, each NIR LED having a peak emission of 3.33 W instead of 2.5 W. The accumulated total peak intensity is still 500 W. Therefore, other related parameters stay the same.

This variation demonstrates that one of the peak emission level of individual radiation devices and the number thereof may vary to accommodate changes in the other, while the same total peak emission is achieved.

Variation 10

In this variation the target peak power density is about 32 mW/cm$^2$ of NIR radiation with 850 nm at the skin. Such intensities (in the upper end of the range of 1-50 mW/cm$^2$ discussed earlier in this disclosure) may be beneficial at specific locations of the human body where a deeper penetration of the radiation is particularly useful.

Research has shown that such power densities are beneficial if the target is the human brain to treat certain diseases such as major depression disorder, Alzheimer disease and dementia. Therefore, such higher intensities may be beneficial in home for the elderly or psychiatric institutions.

Research also has demonstrated that NIR light between 800-1100 nm at such intensities is beneficial to increase concentration and/or focus of healthy subjects, also by targeting the brain with similar power densities described in this variation. Therefore, it might be beneficial in environments with demand for enhanced cognitive functions to use power densities at slightly higher power densities, the benefits of which would more than justify the marginal increase in electrical power consumption. Lamps of this variation with cognitive enhancing properties may be useful for schools, universities, offices, meeting rooms, stages or other locations with similar requirements.

Assume a 150 cm linear lamp with homogeneous light distribution over 180°. At a distance r=2 m from the lamp, the surface of a theoretical half-cylinder, which represents the theoretical light distribution at the distance of 2 m, is A=πrh=about 10 m$^2$. This results in 1 m$^2$ per 0.2 W if continuous wave NIR output power is 2 W.

Assume also that the linear lamps are commonly placed in grids. Hence, the cumulative average power density on the skin of the user at 2 m average distance from the linear lamps is estimated to be on average 60% higher, which results in about 32 uW/cm$^2$. This is 1000 times lower than the desired target of 32 mW/cm$^2$ and indicates that the (peak) NIR output power at the radiation source should be 1000 times of 2 W, i.e., 2000 W.

If the NIR radiation source is pulsed at a pulse duration of 1 ms and a pulse period of 1 s, which amounts to a duty cycle of 0.1%, then the NIR radiation source still achieves a peak emission power of 2000 W during the pulses but the average electrical power consumption over time decreases by a factor of 1000 (i.e., equivalent to 2 W continuous-wave (CW)).

Assume that the 1.5 m length can accommodate 200 NIR LEDs spread out, which brings the desired single LED peak intensity down to 10 W (at 1 ms/s pulses). This may be implemented by, for example, laser LEDs, which can withstand more shorter and stronger pulses over the lifetime.

The resulting dosage after 8 hours to the user at a 2-meter distance is about 32 (uW/cm$^2$)*8 (hours)*60 (minutes/hour) *60 (seconds/minute)=921600 (uJ/cm$^2$)=0.9216 (J/cm$^2$).

The NIR radiation source would consume 4 W of electrical power. If the lamp comprises visible light sources for general lighting that consume 30 W, then the total electrical consumption of the lamp of this variation would be 34 W.

Example—"Rejuvenation Mirror"

PBM-inducing radiation may be added to a mirror. This may, for example, add PBM to the morning routine.

Assume a NIR LED with homogeneous light distribution in a half-sphere (the calculation method explained below may be adapted for other distribution patterns such as a focused pattern or a Lambertian pattern). At a distance $r$ from the lamp, the surface area of the half-sphere is $A=2\pi r^2$. For example, if the average distance r is 0.66 m, then A is about 27370 $cm^2$.

Assume that about an NIR power density of 8 $mW/cm^2$ over 800-870 nm is desired on the skin. Then, the radiation source should emit an NIR emission over 800-870 nm with an optical power of about 8 $mW/cm^2 * 27370$ $(cm^2)$=about 219 W. (In terms of useful NIR emission, this is roughly equivalent to 20 pieces of 100 W incandescent bulbs mounted around the mirror with reflector.)

Techniques in adjusting the radiation patterns (such as favorable Lambertian emission or optically focused LED emission) may bring the required emission power at the radiation source down from 219 W to 100 W. This may be implemented, for example, by 100 NIR LEDs, each having 1 W peak emission at 850 nm with 30 nm FWHM.

The 100 NIR LEDs may be pulsed at a pulse duration of 10 ms and a pulse frequency of 10 Hz (i.e., the LEDs are switched on 10 ms for every 0.1 s, equivalent to a total on-time of 100 ms/s). The resulting electrical power consumption, assuming an WPE of the NIR light source of 50%, would be 20 W. The delivered dosage to the surface of the skin at the distance r would be 48 $mJ/cm^2$ per minute. Assume that the user uses the mirror 20 min a day. Then the mirror would be delivering an average energy density (or dose, fluence) of about 1 $J/cm^2$ per day to the exposed skin at the above-mentioned distance r.

As additional feature, the NIR radiation source of the mirror may be switched on by awareness sensor(s) or motion sensor(s).

Variation—Inpatient Lighting

The same concept may also be applied for inpatient lighting in hospitals (such as HCL (Human centric lighting) elements at the end wall of patient beds).

Assume a setup similar to the Rejuvenation Mirror example described above, in which 100 NIR LEDs with the same light properties are located at an average distance of 0.66 m from the patient's face. The device may be designed to automatically turn on 1-2 times a day for 20-100 minutes, delivering each time 1-5 $J/cm^2$.

Example—Office Lighting Troffer

A troffer is a rectangular light fixture that fits into a modular dropped ceiling grid (i.e., 600×600 mm, or 300×1200 mm). Troffer fixtures may be designed to accommodate standard fluorescent lamps (e.g., T12, T8 or T5) or to have integral LED sources. Troffers may be recessed sitting above the ceiling grid or available in surface mount 'boxes'.

In this example, a popular troffer named "Belvision C1 600 CDP LED3900 nw 01" from the company Trilux is used. It is assumed that the troffer is mounted in a room having the size 5×4×3 m. To achieve a standard illuminance of >500 lux on an assumed working surface 75 cm above the floor, we need 3 (rounded up from exactly 2.93) fixtures, at a surface reflectivity of 70 (ceiling)/50(walls)/20(floor) % and a maintenance factor of 0.8. FIG. 8 provides an exemplary illustration of the troffer and its usage in such a room.

Each of the troffers have an energy consumption of 27 W, total 81 W for all 3 fixtures. This results in about 4 W electrical energy consumption per $m^2$ working surface, or about 2 W optical per $m^2$ assuming a Wall plug efficiency (WPE) of 50%.

At the above described radiation pattern and surface reflectivity of the room, we achieve 500 lx at the working surface, which can also be described as 500 lumen/$m^2$. The total available Lumen are 12000 lm (4000 lm per fixture), which means that without losses the available lumens are 600 l/$m^2$, which shows that we lose 100 l per $m^2$ due to reflection and absorption losses from the ceiling, walls and the floor. Therefore, in this setup 20% of the initially available lumens emitted by the fixtures are lost.

The next step is to figure out the amount of optical Watts in the NIR spectrum per fixture, assuming similar maintenance and reflection losses and similar radiation patterns for the integrated NIR light.

Assume a target power density of 8 $mW/cm^2$ of NIR radiation with a peak wavelength of 850 nm at a similar distance from the ground compared with the working surface, which is 75 cm above the floor. Factoring in the above described loss of 20% compared with the initially available optical power at the source, we assume that 10 mW per $cm^2$ of the working surface is needed to be radiated, which is 100 W/$m^2$, or 2000 W for the whole cross-sectional area of 20 $m^2$ (5×4 m).

Therefore, we need 2000 W/3 fixtures=about 667 W peak emission at 850 nm per fixture. This peak emission may be enabled by 200 single NIR LEDs per fixture, each having a pulsed peak emission of 3.335 W optical power.

Assume that the NIR light emission has a pulse frequency of 1 Hz and a pulse duration of 1 ms (rectangular waveform, 100% modulation). At such pulsing parameter, the average emitted optical Watts at 850 nm are 0.667 W, or 1.333 W electric power per fixture at 50% WPE, or in total 4 W electric power (for all 3 fixtures) per room.

Further, we assume that a person is exposed in said light for 8 h, or 28800 s, and that the skin surface of said person is on average at a similar distance to the light sources compared with the working surface during this time. Therefore, the achieved dose (or energy density) per day (of 8 h exposure) on the surface of the skin of said person is on average 8 $(mW/cm^2)*28800$ $(s)*(1/1000)$=about 0.23 $(J/cm^2)$.

Variation 1

In this variation, we assume that the NIR radiation emission has a pulse frequency of 2 Hz and a pulse duration of 2 ms (rectangular waveform, 100% modulation). At this duty cycle and frequency, the average emitted optical Watts at 850 nm are 4 times higher compared to the above example, which results in 2.667 W, or 5.334 W electric power per fixture at 50% WPE, or in total about 16 W electric power (for all 3 fixtures) per room. Further, we assume that a person is exposed in said light for 8 h, or 28800 s, and that the skin surface of said person is in average at a similar distance to the light sources compared with the working surface during this time. Therefore, the achieved dose (or energy density) per day (8 h exposure) on the surface of the skin of said person is about 0.92 $J/cm^2$ (8 mW*28800 s*(0.002/0.5)).

Variation 2

In this variation, we assume that the NIR radiation has a pulse frequency of 3 Hz and a pulse duration of 3 ms (rectangular waveform, 100% modulation). At this duty cycle and frequency, the average emitted optical Watts at 850 nm are 9 times higher compared to the example, which results in 6 W optical power, or 12 W electric power per fixture at 50% WPE, or in total 36 W electric power (for all 3 fixtures) per room. Further, we assume that a person is exposed to said radiation for 8 h, or 28800 s, and that the skin surface of said person is in average at a similar distance to the light sources compared with the working surface during this time. Therefore, the achieved dose (or energy density) per day (8 h exposure) on the surface of the skin of said person is about 2.07 J/cm$^2$ (8 mW*28800 s*0.003*3).

Variation 3

In this variation, we assume that the NIR radiation has a pulse frequency of 1.5 Hz and a pulse duration of 10 ms (rectangular waveform, 100% modulation). At this duty cycle and frequency, the average emitted optical Watts at 850 nm are 15 times higher compared to the example, which results in 10 W optical power, or 20 W electric power per fixture at 50% WPE, or in total 60 W electric power (for all 3 fixtures) per room. Further, we assume that a person is exposed in said light for 8 h, or 28800 s, and that the skin surface of said person is in average at a similar distance to the light sources compared with the working surface during this time. Therefore, the achieved dose (or energy density) per day (8 h exposure) on the surface of the skin of said person is about 3.46 J/cm$^2$ (8 mW*28800 s*0.010*1.5).

Variation 4

In this variation, we assume that the NIR radiation has a pulse frequency of 0.1 Hz and a pulse duration of 5 ms (rectangular waveform, 100% modulation). At this duty cycle and frequency, the average emitted optical Watts at 850 nm are 2 times lower compared to the example, which results in 0.333 W optical power, or 0.667 W electric power per fixture at 50% WPE, or in total 2 W electric power (for all 3 fixtures) per room. Further, we assume that a person is exposed in said light for 8 h, or 28800 s, and that the skin surface of said person is on average at a similar distance to the light sources compared with the working surface during this time. Therefore, the achieved dose (or energy density) per day (8 h exposure) on the surface of the skin of said person is about 0.115 J/cm$^2$ (8 mW*28800 s*0.005*0.1).

Example—Lighting Troffer

Another example of a lighting troffer with implementation details is provided below.

Figure 9A:
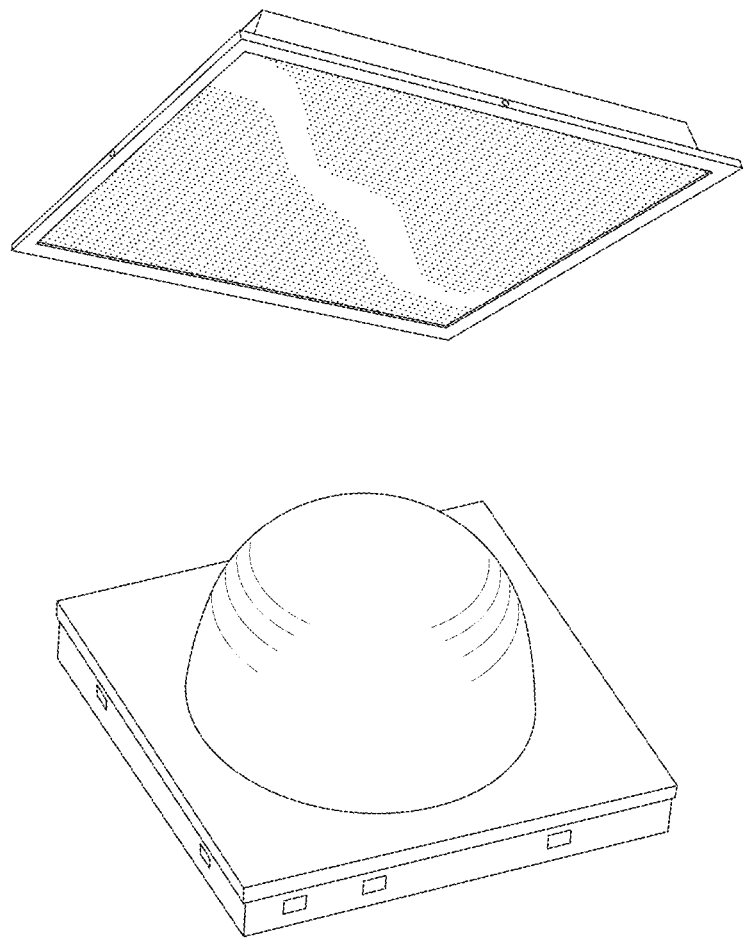
FIG. 9A shows examples of a visible light source and a radiation source that may be used in embodiments of the present disclosure.

FIG. 9A shows the visible light source and the radiation source used in this example. The top part of FIG. 9A shows a SYLVANIA START PANEL 600 4000K G4" (EAN 5410288477794) with the following specifications. The 596×65×596 mm panel is equipped with LEDs to produce visible light at a color temperature of 4000K and a luminous flux of 4200 lm. The panel operates at 230 V and consumes 30 W of electrical power. There is a diffusor of PMMA/PVA that is about 1.5 mm thick.

The lighting troffer is also equipped with 100 LEDs emitting infrared radiation from Vishay (Type VSMY98545). The bottom part of FIG. 9A shows a picture of one such LED. The package form is high power SMD with lens. The dimension is 3.85×3.85×2.24 (L×W×H in mm). The peak wavelength is λp=850 nm. The angle of half intensity is (ϕ)=45°.

The design target is at least 160 W of optical power at the 850 nm peak so as to realize 8 mW/cm$^2$ power density in the desired spectrum NIR-A at a distance of about 2 m, with the angle of half intensity of 45° factored in.

According to the datasheet of VSMY98545 (which may be found at https://www.vishay.com/doc?81223), each LED outputs about 800 mW optical power at 1 A of forward current, or about 1.89 W at 2.5 A of forward current and pulsed at 5 ms with a duty cycle of 1% (800 mW multiplied by about 236%, derived from the datasheet). Thus, 100 such LEDs placed in the visible lighting panel (behind its diffusor) may output 189 W in total, thereby meeting the design target.

Figure 9B:
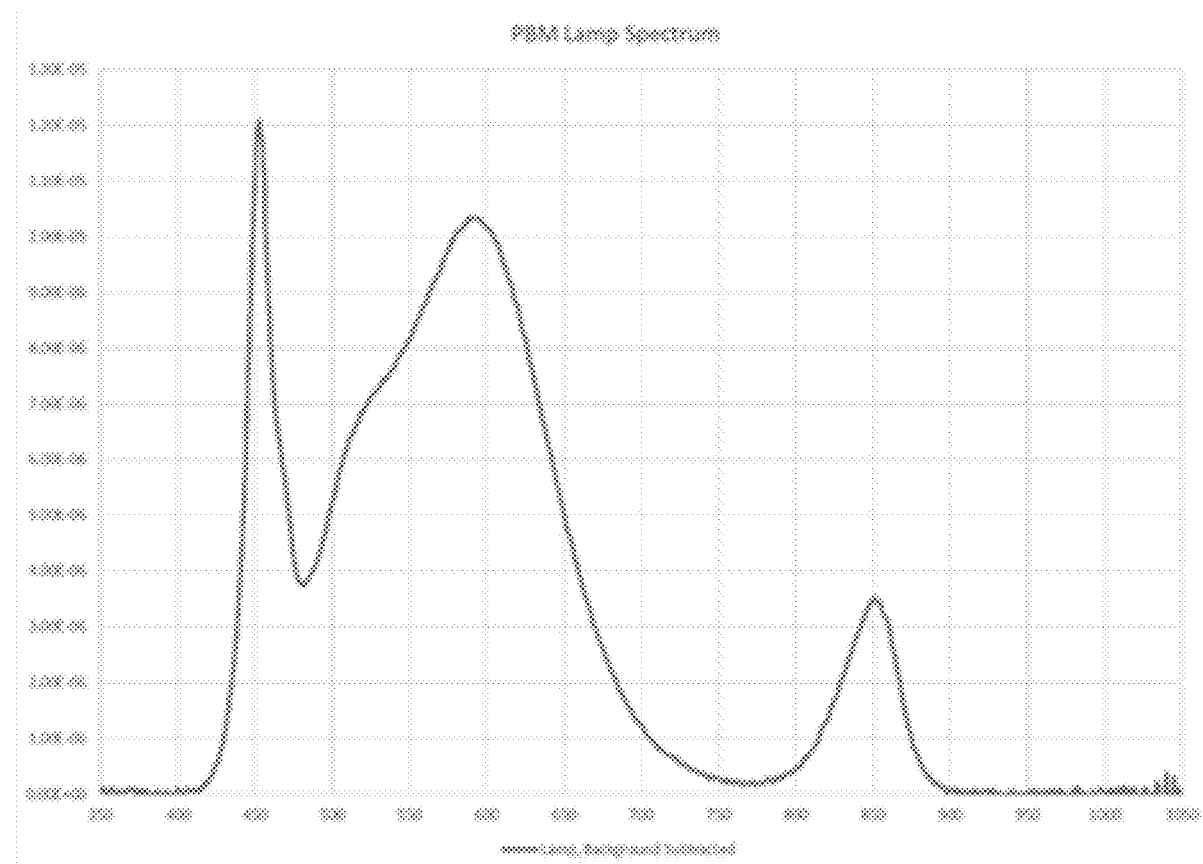
FIG. 9B illustrates a measured spectrum of the visible light source used in an embodiment of the present disclosure, the measurement averaged over 4 seconds.

FIG. 9B illustrates a spectrum measured at 1 meter from the lighting troffer of this example in the center of direction of light emission. The measurement was done in a dark lab, with background noise measured separately and subtracted from the measured spectrum. The measurement was performed over 4 seconds with the measured spectrum averaged to ensure that a sufficiently large number of pulse periods were included and to measure the average optical intensity in the pulsed part of the total spectrum. The integral power in the near infrared portion between 760-900 nm is roughly 10% of the optical power in the visible spectrum. The percentage matches the fact that the electrical power fed to the infrared LEDs is about 15% of that of the visible light panel and that the infrared LEDs has an electrical efficiency of about 40% compared to the electrical efficiency of about 60% of the visible light panel. The ratio of the electrical power fed to the infrared LEDs to that fed to the visible light panel is calculated as 2.0 (VF from FIG. 3 of the datasheet) *2.5 (A)*1% (duty cycle)*100 (number LEDs)/30 (W), which is 16.66% and close to 15%.

This example irradiates the surface of its user at a 2 m distance with an average dosage (fluence) of 4.6 J/cm$^2$ per 8 hours in the spectrum between 760 and 900 nm, assuming 160 W of optical output (lower than 189 W due to the diffusor loss) divided over a spherical surface area of a 45° 3-dimensional cone at 2 m away from the lighting troffer.

It should be noted that the above-described examples and variations are not limiting.

In sum, the present disclosure provides at least a lighting arrangement, a lighting method, and a lamp for general lighting, a retrofit light bulb for general lighting, a retrofit light tube for general lighting and a luminaire for general lighting. By sophisticated pulsing of the radiation source, an appropriate and beneficial amount of radiation in a predetermined spectrum may be provided at a reasonable amount of power consumption. Combining such radiation source into a general lighting apparatus may greatly expand it use and may turn it into a general lighting source with medical benefits that is easy to use. Pulsing the radiation source may also help prevent overdosage if the user is exposed to radiation in the predetermined spectrum for an extended period of time, such as more than 20 minutes.

The descriptions above are intended to be illustrative, not limiting. It will be apparent to the person skilled in the art that alternative and equivalent embodiments of the invention can be conceived and reduced to practice, without departing from the scope of the claims set out below.

REFERENCE SIGNS LIST

1*a* lighting arrangement
1*b* lighting arrangement 1c lighting arrangement
10 radiation source
11 light source
12 driver circuit
13 driver circuit
14 sensor
100 radiation
101 first driving current
110 visible light
111 second driving current
141 input
20 user
2a (retrofit) bulb
2b (retrofit) light tube
2c lamp
2d luminaire
30 curve
31 curve
32 curve
33 curve
40 curve
41 curve
7 linear lamp
70 LED
71 LED

What is claimed is:

1. A lighting arrangement for general lighting, comprising:
 a light source capable of emitting visible light suitable for general lighting, the visible light being white light;
 a radiation source capable of emitting radiation in a predetermined spectrum, wherein the predetermined spectrum is in a range 760-1400 nm; and
 a driver circuit capable of providing a first driving current that is pulsed;
 wherein the lighting arrangement is configured to provide the first driving current to the radiation source but not the light source; and
 wherein, in use, the light source is configured to emit at least 250 lumens,
 wherein a peak emission power of the radiation source receiving the pulsed first driving current enables a power density of 0.4-50 mW/cm$^2$, measured at a common average distance of between 0.2 and 5 m from the radiation source.

2. The lighting arrangement of claim 1, wherein the light source is capable of emitting white light having a color point in a CIE XYZ color space, wherein the color point has a distance less than 10 Standard Deviation Color Matching to a black body line in said color space.

3. The lighting arrangement of claim 1, wherein the lighting arrangement is configured to provide a second driving current different from the first driving current to the light source, wherein the second driving current is a direct current, or an alternating current, or a pulse-width modulated current having a pulse frequency in a range 20 kHz-300 kHz.

4. The lighting arrangement of claim 1, wherein the driver circuit is a first driver circuit, and wherein the lighting arrangement further comprises a second driver circuit adapted to provide a second driving current.

5. The lighting arrangement of claim 1, wherein the first driving current has a duty cycle of not greater than 20%.

6. The lighting arrangement of claim 1, wherein the radiation source is configured to operate at an enhanced permissible driving current; or wherein at least one of the pulse duration, the pulse frequency and the duty cycle are so selected as to enable the first driving current to drive the radiation source at an enhanced permissible driving current.

7. The lighting arrangement of claim 1, wherein the predetermined spectrum of the radiation source does not include a visible spectrum.

8. The lighting arrangement of claim 1, wherein the predetermined spectrum of the radiation source is in the range 800-1100 nm.

9. The lighting arrangement of claim 1, wherein a peak emission power of the radiation emitted by the radiation source energized by the pulsed first driving current is at least 25 W.

10. The lighting arrangement of claim 1, wherein the radiation source receiving the pulsed first driving current is capable of delivering a dosage of 0.01-5 J/cm$^2$ measured at a common average distance from the radiation source, wherein the common average distance from the radiation source is between 0.2 and 5 m.

11. The lighting arrangement of claim 1, wherein the radiation source receiving the pulsed first driving current is capable of delivering a dosage of 0.01-5 J/cm$^2$ measured at a distance where an illuminance of the lighting arrangement is about 500 Lux.

12. The lighting arrangement of claim 1, wherein the radiation source in use consumes electrical power of less than 50 W RMS; or wherein the radiation source in use consumes electrical power per square meter of an irradiated surface of less than 10 W RMS.

13. The lighting arrangement of claim 1, wherein the lighting arrangement is adapted to generate visible light from the light source having a luminous flux which does not have an %-flicker of more than 40% when the light source is in use.

14. The lighting arrangement of claim 1, wherein a ratio of an electrical power consumed by the radiation source to an electrical power consumed by the light source when the lighting arrangement is in use is not greater than 50%.

15. A luminaire for general lighting comprising a lighting arrangement of claim 1.

16. The lighting arrangement of claim 1, wherein the lighting arrangement comprises a lamp, or a retrofit light bulb, or a retrofit light tube.

17. A lighting arrangement for general lighting, comprising:
 a light source capable of emitting visible light suitable for general lighting, the visible light being white light:
  a radiation source capable of emitting radiation in a predetermined spectrum, wherein the predetermined spectrum is in a range 760-1400 nm; and
 a driver circuit capable of providing a first driving current that is pulsed;
  wherein the lighting arrangement is configured to provide the first driving current to the radiation source but not the light source; and
  wherein, in use, the light source is configured to emit at least 250 lumens,
 wherein a peak emission power of the radiation source receiving the pulsed first driving current enables a power density of 0.4-50 mW/cm$^2$, measured at a distance where an illuminance of the lighting arrangement is about 500 Lux.

18. A lighting method comprising:
 providing a light source capable of emitting visible light suitable for general lighting, the visible light being white light;

providing a radiation source capable of emitting radiation in a predetermined spectrum, wherein the predetermined spectrum is in a range 760-1400 nm;

supplying a first driving current that is pulsed to the radiation source to generate the radiation in the predetermined spectrum;

wherein the first driving current is not supplied to the light source; and wherein, in use, the light source is configured to emit at least 250 lumens, wherein a peak emission power of the radiation source receiving the pulsed first driving current enables a power density of 0.4-50 mW/cm$^2$, measured at a common average distance of between 0.2 and 5 m from the radiation source.

19. The lighting method of claim 18, wherein the radiation source receiving the pulsed first driving current is capable of delivering a dosage of 0.01-5 J/cm$^2$ measured at a common average distance from the radiation source, wherein the common average distance from the radiation source is between 0.2 and 5 m.

20. The lighting method of claim 18, wherein the radiation source receiving the pulsed first driving current is capable of delivering a dosage of 0.01-5 J/cm$^2$ measured at a distance where an illuminance of the lighting arrangement is about 500 Lux.

21. A lighting arrangement comprising:
a light source capable of emitting visible light, the visible light being white light;
a radiation source capable of emitting radiation in a predetermined spectrum, wherein the predetermined spectrum is in a range 760-1400 nm; and
a driver circuit adapted to provide a first driving current that is pulsed;
wherein the lighting arrangement is adapted to provide the first driving current to the radiation source but not the light source; and
wherein, in use, the light source is configured to emit at least 25 lumens,
wherein a peak emission power of the radiation source receiving the pulsed first driving current enables a power density of 0.4-50 mW/cm$^2$, measured at a common average distance of between 0.2 and 5 m from the radiation source.

22. The lighting arrangement of claim 21, wherein the radiation source receiving the pulsed first driving current is capable of delivering a dosage of 0.01-5 J/cm$^2$ measured at a common average distance from the radiation source, wherein the common average distance from the radiation source is between 0.2 and 5 m.

23. The lighting arrangement of claim 21, wherein the radiation source receiving the pulsed first driving current is capable of delivering a dosage of 0.01-5 J/cm$^2$ measured at a distance where an illuminance of the lighting arrangement is about 500 Lux.

24. A lighting method comprising:
providing a light source capable of emitting visible light suitable for general lighting, the visible light being white light;
providing a radiation source capable of emitting radiation in a predetermined spectrum, wherein the predetermined spectrum is in a range 760-1400 nm;
supplying a first driving current that is pulsed to the radiation source to generate the radiation in the predetermined spectrum;
wherein the first driving current is not supplied to the light source; and wherein, in use, the light source is configured to emit at least 250 lumens, wherein a peak emission power of the radiation source receiving the pulsed first driving current enables a power density of 0.4-50 mW/cm$^2$, measured at a distance where an illuminance of the lighting arrangement is about 500 Lux.

25. A lighting arrangement comprising:
a light source capable of emitting visible light, the visible light being white light;
a radiation source capable of emitting radiation in a predetermined spectrum, wherein the predetermined spectrum is in a range 760-1400 nm; and
a driver circuit adapted to provide a first driving current that is pulsed;
wherein the lighting arrangement is adapted to provide the first driving current to the radiation source but not the light source; and
wherein, in use, the light source is configured to emit at least 25 lumens, wherein a peak emission power of the radiation source receiving the pulsed first driving current enables a power density of 0.4-50 mW/cm$^2$, measured at a distance where an illuminance of the lighting arrangement is about 500 Lux.

* * * * *